US012612457B2

(12) United States Patent
Tsukerman et al.

(10) Patent No.: US 12,612,457 B2
(45) Date of Patent: *Apr. 28, 2026

(54) HUMANIZED ANTIBODIES AGAINST NECTIN-2 AND DRUG CONJUGATES THEREOF

(71) Applicant: Nectin Therapeutics Ltd., Jerusalem (IL)

(72) Inventors: Pinchas Tsukerman, Jerusalem (IL); Anas Atieh, Jerusalem (IL); Akram Obiedat, Jerusalem (IL); Guy Cinamon, Tel Aviv (IL)

(73) Assignee: Nectin Therapeutics Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/818,412

(22) Filed: Aug. 28, 2024

(65) Prior Publication Data

US 2024/0424128 A1 Dec. 26, 2024

Related U.S. Application Data

(63) Continuation of application No. PCT/IL2023/050203, filed on Feb. 27, 2023.
(Continued)

(51) Int. Cl.
*C07K 16/28* (2006.01)
*A61K 39/00* (2006.01)
(Continued)

(52) U.S. Cl.
CPC .... *C07K 16/2803* (2013.01); *A61K 47/68031* (2023.08); *A61K 47/68037* (2023.08);
(Continued)

(58) Field of Classification Search
None
See application file for complete search history.

(56) References Cited

U.S. PATENT DOCUMENTS 4,816,567 A 3/1989 Cabilly et al.
4,946,778 A 8/1990 Ladner et al.
(Continued)

FOREIGN PATENT DOCUMENTS

CN 108473572 A 8/2018
CN 108513576 A 9/2018
(Continued)

OTHER PUBLICATIONS

Yaghoubi et al. Petential drugs used in the antibody-drug conjugate (ADC) architecture for cancer therapy. J Cell Physiol. 2020; 235: 31-64. DOI: 10.1002/jcp.28967 (Year: 2020).*
(Continued)

*Primary Examiner* — Amy E Juedes
*Assistant Examiner* — Hilary Ann Petrash
(74) *Attorney, Agent, or Firm* — Antheros Legal Advisors LLP

(57) ABSTRACT

The present invention provides humanized monoclonal antibodies that recognize human Nectin-2 with high affinity and specificity and inhibit its binding to CD112R. These antibodies carry cytotoxic payload and do not interact with Fc gamma receptors. The present invention further provides pharmaceutical compositions comprising the antibodies and methods for their use in cancer immunotherapy.

6 Claims, 17 Drawing Sheets

Specification includes a Sequence Listing.

Related U.S. Application Data

(60) Provisional application No. 63/314,490, filed on Feb. 28, 2022.

(51) Int. Cl.
    *A61K 47/68*     (2017.01)
    *A61P 35/00*     (2006.01)
    *G01N 33/574*     (2006.01)

(52) U.S. Cl.
    CPC .......... *A61K 47/6849* (2017.08); *A61P 35/00* (2018.01); *G01N 33/57484* (2013.01); *A61K 2039/505* (2013.01); *C07K 2317/24* (2013.01); *C07K 2317/73* (2013.01); *C07K 2317/92* (2013.01); *C07K 2317/94* (2013.01)

(56) References Cited

U.S. PATENT DOCUMENTS

| | | | |
|---|---|---|---|
| 5,225,539 A | 7/1993 | Winter | |
| 5,530,101 A | 6/1996 | Queen et al. | |
| 5,585,089 A | 12/1996 | Queen et al. | |
| 5,641,870 A | 6/1997 | Rinderknecht et al. | |
| 5,693,761 A | 12/1997 | Queen et al. | |
| 5,693,762 A | 12/1997 | Queen et al. | |
| 2010/0008928 A1 | 1/2010 | Sato et al. | |
| 2017/0037133 A1 | 2/2017 | Fiedler et al. | |
| 2018/0185480 A1 | 7/2018 | Mandelboim et al. | |

FOREIGN PATENT DOCUMENTS

| | | | |
|---|---|---|---|
| CN | 109071666 A | 12/2018 | |
| EP | 0404097 A2 | 12/1990 | |
| WO | WO-1986001533 A1 | 3/1986 | |
| WO | WO-1990007861 A1 | 7/1990 | |
| WO | WO-1992022653 A1 | 12/1992 | |
| WO | WO-1993011161 A1 | 6/1993 | |
| WO | WO-199315210 A1 | 8/1993 | |
| WO | WO-199613583 A2 | 5/1996 | |
| WO | WO-199637621 A2 | 11/1996 | |
| WO | WO-2003080672 A1 | 10/2003 | |
| WO | WO-2007043635 A1 | 4/2007 | |
| WO | WO-2008126847 A1 | 10/2008 | |
| WO | WO-2017021526 A1 | 2/2017 | |
| WO | WO-2017041004 A1 | 3/2017 | |
| WO | WO-2017149538 A1 | 9/2017 | |
| WO | WO-2017189963 A1 | 11/2017 | |
| WO | WO-2020144697 A1 | 7/2020 | |
| WO | WO-2023161943 A1 | 8/2023 | |

OTHER PUBLICATIONS

Anaya, J., et al., OncoLnc: linking TCGA survival data to mRNAs, miRNAs, and lncRNAs, Peer J Comp Sci, 2: e67, pp. 1-13 (2016).

Badri, H., et al., Optimization of radiation dosing schedules for proneural glioblastoma, J Math Biol, 72(5): 1301-1336 (2016).

Baylot, V., et al., TCTP Has a Crucial Role in the Different Stages of Prostate Cancer Malignant Progression, Results Probl Cell Differ, 64: 255-261 (2017).

Bird, R.E., et al., Single-chain antigen-binding proteins, Science, 242(4877): 423-426 (1988).

Brennan, M., et al., Preparation of bispecific antibodies by chemical recombination of monoclonal immunoglobulin G1 fragments, Science, 229(4708): 81-83 (1985).

Carter, P., et al., High level *Escherichia coli* expression and production of a bivalent humanized antibody fragment, Biotechnology (NY), 10(2): 163-167 (1992).

Clakson, T., et al., Making antibody fragments using phage display libraries, Nature, 352(6336): 624-628 (1991).

Deng, H-P., et al., Preparation and characterization of monoclonal antibodies against human CD112 (Nectin2/PRR2), Chinese Journal of Cellular and Molecular Immunology, 23(4): 356-358, Abstract (2007).

Fields, C., et al., Creation of recombinant antigen-binding molecules derived from hybridomas secreting specific antibodies, Nat Protoc, 8(6): 1125-1148 (2013).

Gao, Q., et al., Therapeutic potential of CRISPR/Cas9 gene editing in engineered T-cell therapy, Cancer Med, 8(9): 4254-4264 (2019).

Holliger, P., et al., "Diabodies": small bivalent and bispecific antibody fragments, Proc Natl Acad Sci USA, 90(14): 6444-6448 (1993).

Huston, J.S., et al., Protein engineering of antibody binding sites: recovery of specific activity in an anti-digoxin single-chain Fv analogue produced in *Escherichia coli*, Proc Natl Acad Sci USA, 85(16): 5879-5883 (1988).

Köhler, G., et al., Continuous cultures of fused cells secreting antibody of predefined specificity, Nature, 256(5517): 495-497 (1975).

Lefranc, M-P., et al., IMGT unique numbering for immunoglobulin and T cell receptor variable domains and Ig superfamily V-like domains, Dev Comp Immunol, 27(1): 55-77 (2003).

Marks, J.D., et al., By-passing immunization. Human antibodies from V-gene libraries displayed on phage, J Mol Biol, 222(3): 581-597 (1991).

Morimoto, K., et al., Single-step purification of F(ab')2 fragments of mouse monoclonal antibodies (immunoglobulins G1) by hydrophobic interaction high performance liquid chromatography using TSKgel Phenyl-5PW, J Biochem Biophys Methods, 24(1-2): 107-117 (1992).

Morrison, S.L., et al., Chimeric human antibody molecules: mouse antigen-binding domains with human constant region domains, Proc Natl Acad Sci USA, 81(21): 6851-6855 (1984).

Muller, S., et al., Spliceosomal peptide P140 for immunotherapy of systemic lupus erythematosus: results of an early phase II clinical trial, Arthritis Rheum, 58(12): 3873-3883 (2008).

Newick, K., et al., CAR T Cell Therapy for Solid Tumors, Annu Rev Med, 68: 139-152 (2017).

Oshima, T., et al., Fc engineering of anti-Nectin-2 antibody improved thrombocytopeniadverse event in monkey, PLoS One, 13(5): e0196422 (2018).

Oshima, T., et al., Nectin-2 is a potential target for antibody therapy of breast and ovarian cancers, Mol Cancer, 12:60, pp. 1-13 (2013).

Park, M-H., et al., Pharmacokinetic and Metabolism Studies of Monomethyl Auristatin F via Liquid Chromatography-Quadrupole-Time-of-Flight Mass Spectrometry, Molecules, 24(15): 2754 (2019).

PCT/IL2020/050047 International Search Report and Written Opinion mailed May 7, 2020.

PCT/IL2023/050203 International Search Report and Written Opinion mailed May 30, 2023.

Rudikoff, S., et al., Single amino acid substitution altering antigen-binding specificity, Proc Natl Acad Sci USA, 79(6): 1979-1983 (1982).

Scarano, S., et al., Surface plasmon resonance imaging for affinity-based biosensors, Biosens Bioelectron, 25(5): 957-966 (2010).

Stamm, H., et al., Immune checkpoints PVR and PVRL2 are prognostic markers in AML and their blockade represents a new therapeutic option, Oncogene, 37(39): 5269-5280 (2018).

Stamm, H., et al., Interaction of PVR/PVRL2 with TIGIT/DNAM-1 as a novel immune checkpoint axis and therapeutic target in cancer, Mamm Genome, 29(11-12): 694-702 (2018).

Tamura, M., et al., Structural correlates of an anticarcinoma antibody: identification of specificity-determining residues (SDRs) and development of a minimally immunogenic antibody variant by retention of SDRs only, J Immunol, 164(3): 1432-1441 (2000).

Ward, E.S., et al., Binding activities of a repertoire of single immunoglobulin variable domains secreted from *Escherichia coli*, Nature, 341(6242): 544-546 (1989).

Wu., T.T., et al., An analysis of the sequences of the variable regions of Bence Jones proteins and myeloma light chains and their implications for antibody complementarity, J Exp Med, 132(2): 211-250 (1970).

Zapata, G., et al., Engineering linear F(ab')2 fragments for efficient production in *Escherichia coli* and enhanced antiproliferative activity, Protein Eng, 8(10): 1057-1062 (1995).

(56)     References Cited

OTHER PUBLICATIONS

Zhu, Y., et al., Identification of CD112R as a novel checkpoint for human T cells, J Exp Med, 213(2): 167-176 (2016).

* cited by examiner

HUMANIZED ANTIBODIES AGAINST NECTIN-2 AND DRUG CONJUGATES THEREOF

CROSS-REFERENCE

This application is a continuation of International Application No. PCT/IL2023/050203, filed Feb. 27, 2023, which claims the benefit of and priority to U.S. Provisional Application No. 63/314,490, filed Feb. 28, 2022, each of which is incorporated by reference in its entirety herein.

SEQUENCE LISTING

The contents of the electronic sequence listing (IMNM-402WOC1_SL.xml; Size: 74,801 bytes; and Date of Creation: Feb. 27, 2023) is herein incorporated by reference in its entirety.

FIELD OF THE INVENTION

The invention is in the field of immunotherapy and relates to anti-Nectin-2 antibodies and antibody-conjugates and to therapeutic and diagnostic compositions comprising them, for treating diseases, particularly cancer.

BACKGROUND OF THE INVENTION

Cancer immunotherapy is utilized for generating and augmenting an anti-tumor immune response, e.g., by treatment with antibodies specific to antigens on tumor cells, or by specific activation of anti-tumor T cells. The ability of recruiting immune cells (e.g., T cells) against tumor cells in a patient provides a therapeutic modality of fighting cancer types and metastasis that are otherwise considered incurable.

T cell mediated immune responses include multiple sequential steps regulated by a balance between co-stimulatory and co-inhibitory signals that control the magnitude of the immune response. The inhibitory signals, referred to as immune checkpoints, are crucial for the maintenance of self-tolerance and for the limitation of immune-mediated collateral tissue damage. These inhibitory signals affect the response of T cells and re-shape the immune response.

Nectin-2, which was also named Poliovirus Receptor-Related Protein-2, Poliovirus Receptor-Like 2, CD112, or PRR-2, is a single pass transmembrane glycoprotein with two Ig-like C2-type domains and an Ig-like V-type domain. Nectin-2 is involved in mediating cell adhesion to extracellular matrix molecules, serving as one of the plasma membrane components of adherent junctions. It also serves as an entry receptor for certain mutant strains of herpes simplex virus and pseudorabies virus, and it is involved in cell to cell spreading of these viruses. Variations in this gene have been associated with differences in the severity of multiple sclerosis. Importantly, Nectin-2 can also serve as a modulator of T-cell signaling. It can be either a co-stimulator, or a co-inhibitor of T-cell functions, depending on the receptor it binds on these target cells: upon binding to CD226 (DNAM-1), it stimulates T-cell proliferation and cytokine production, including that of IL-2, and IFN$\gamma$, while upon interaction with PVRIG (CD112R), and/or TIGIT (T-cell immunoreceptor with immunoglobulin and ITIM domains) it inhibits T-cell proliferation and activation. These contradictory interactions are competitive.

Nectin-2 was shown to be overexpressed in various tumors, including breast and ovarian cancers (Oshima et al. Molecular Cancer, 2013, 12:60). The presence of Nectin-2 on tumor cells leads to poor prognosis and reduced activity of T cells (Stamm et al. Oncogene (2018) 37:5269-5280).

US patent application No. 2017/0037133 discloses inhibitors (e.g., antibodies) against CD112 (Nectin-2, PVRL2), CD155 (PVR), Galectin-9, TIM-3 and/or TIGIT for use in treatment of a blood-borne cancer, in particular acute myeloid leukemia (AML).

International patent application No. WO 2020/144697 discloses monoclonal antibodies (mAbs) that recognize human Nectin-2 and block the interactions with TIGIT and CD112R, for use treatment of cancer.

Antibody-drug conjugates (ADCs) are a promising tool for both direct tumor cell killing and for the consequent activation of bystander immune cells. These therapeutic entities are composed of mAbs linked to cytotoxic drugs (payloads), and are designed, in principle, to widen the therapeutic window of those drugs by limiting their delivery specifically to cells that express the target antigen, and thus to reduce their systemic exposure and toxicity.

An example of a possible payload is Auristatin, a microtubule-destroying drug. It was derived from marine shell-less mollusk Dolabella *auricularia* called dolastatins. Various derivatives of auristatin have been synthesized, such as monomethyl auristatin E (MMAE) and monomethyl auristatin F (MMAF). MMAE and MMAF were developed by Seattle Genetics and used as payloads for ADCs. MMAF and MMAE have their advantages and disadvantages. MMAE is more membrane-permeable and has a lower IC50 than MMAF. However, MMAF is more hydrophilic and has a lower aggregation tendency to show lower systemic toxicity than MMAE (park et al. Molecules 2019, 24, 2754).

There is an unmet need to provide humanized antibodies recognizing human Nectin-2 that are safe and potent and can be used, either alone or as a targeting tool, for diagnostically and therapeutically uses in diseases involving Nectin-2 expression, e.g., as ADCs in cancer.

SUMMARY OF THE INVENTION

The present invention provides humanized antibodies that specifically bind Nectin-2. The humanized antibodies of the present invention, selected from a larger collection of antibody clones, have improved properties compared to other anti-Nectin-2 antibodies. The present invention further provides, according to some embodiments, conjugates comprising the antibodies and diagnostic or therapeutic agents. In some embodiments, the conjugates comprise a cytotoxic moiety that is targeted by said humanized antibodies to tumor cells presenting the Nectin-2 receptor on their surface.

A large collection of humanized antibodies was produced by combining specific sets of complementarity determining regions (CDR) sequences and human framework (FW) sequences and introducing specific mutations in these sequences to produce antibodies with modified variable regions and improved properties. Advantageously, the newly designed humanized variable regions described herein preserve the residues critical for the maintenance of the antibody's conformation and binding affinity, while having lower incidence of potential T cell epitopes, thus minimizing the risk of adverse immune response towards the antibodies. The antibodies disclosed herein were designed based on factors including homology, T-cell epitopes, key residues, and predicted structures. Unexpectedly, the humanized antibodies disclosed herein show improved biostability compared with the parental chimeric antibody.

The humanized antibodies disclosed herein were found to be highly suitable for use as targeted anti-cancer therapy with therapeutic toxins. It is now disclosed that the anti-Nectin-2 monoclonal humanized antibody described herein, conjugated to a cytotoxic moiety, exhibit robust killing of various tumor cell lines. The direct targeting of toxins using the antibodies described herein has the potential to increase the anti-tumor efficacy of these toxins, reducing their systemic toxicity, and thus improving the survival of cancer patients.

Human Fc receptors (FcγRs) activate Fc-effector functions such as antibody-dependent cellular cytotoxicity (ADCC) and antibody dependent cellular phagocytosis (ADCP). Some of the ADCs of the present invention comprise one or more Fc mutations that significantly reduce their binding by FcγR that are expressed on immune cells, thereby increasing their safety and specificity. It is now disclosed that ADCs comprising anti-Nectin-2 monoclonal humanized antibody having specific Fc mutations and linked to toxins are highly effective and safe, suitable for anti-cancer therapy.

The inventors of the present invention have shown for the first time that ADCs targeted to Nectin-2 are highly useful for treating cancer, in particular solid tumors.

According to a first aspect, the present invention provides a humanized antibody that specifically binds human Nectin-2, or a fragment thereof comprising at least the antigen binding site, wherein the antibody or a fragment thereof comprises a heavy chain (HC) and a light chain (LC), wherein the heavy chain comprises a variable region having an amino acid sequence at least about 90% identical to a sequence selected from the group consisting of SEQ ID NO: 11, SEQ ID NO: 13, SEQ ID NO: 14, SEQ ID NO: 15 and SEQ ID NO: 16; and wherein the light chain comprises a variable region having an amino acid sequence at least about 90% identical to a sequence selected from the group consisting of SEQ ID NO: 12, SEQ ID NO: 17, SEQ ID NO: 18, SEQ ID NO: 19 and SEQ ID NO: 20.

According to some embodiments, the humanized antibody or a fragment thereof comprises a heavy chain and a light chain, wherein the heavy chain comprises a variable region having an amino acid sequence at least about 90% identical to SEQ ID NO: 11, and the light chain comprises a variable region having an amino acid sequence at least about 90% identical to SEQ ID NO: 12.

According to some embodiments, the humanized antibody or a fragment thereof comprises a heavy chain and a light chain, wherein the heavy-chain variable region comprises the sequence set forth in SEQ ID NO: 11, and the light-chain variable region comprises the sequence set forth in SEQ ID NO: 12.

There are several methods known in the art for determining the CDR sequences of a given antibody molecule, but there is no standard unequivocal method. Determination of CDR sequences from antibody heavy and light chain variable regions can be made according to any method known in the art, including but not limited to the methods known as KABAT, Chothia and IMGT. A selected set of CDRs may include sequences identified by more than one method, namely, some CDR sequences may be determined using KABAT and some using IMGT, for example. According to some embodiments, the CDR sequences of the mAb variable regions are determined using the IMGT method.

According to some embodiments, the humanized antibody or a fragment thereof comprises a set of six CDR sequences, wherein heavy-chain CDR1 comprising the sequence SYW, heavy-chain CDR2 comprising the sequence VYPGNSDS (SEQ ID NO: 8), heavy-chain CDR3 comprising the sequence LVGTFDY (SEQ ID NO: 3), light-chain CDR1 comprising the sequence QNVGIN (SEQ ID NO: 10), light-chain CDR2 comprising the sequence SAS, and light-chain CDR3 comprising the sequence QQYNTNPFT (SEQ ID NO: 6).

According to some embodiments, the humanized antibody or a fragment thereof comprises a set of six CDR sequences, wherein heavy-chain CDR1 comprising the sequence SYWIH (SEQ ID NO: 1), heavy-chain CDR2 comprising the sequence AVYPGNSDSNYNQKF (KA/QG) (SEQ ID NO: 2), heavy-chain CDR3 comprising the sequence LVGTFDY (SEQ ID NO: 3), light-chain CDR1 comprising the sequence (K/R) ASQNVGINV (V/A) (SEQ ID NO: 4), light-chain CDR2 comprising the sequence SASYRYS (SEQ ID NO: 5), and light-chain CDR3 comprising the sequence QQYNTNPFT (SEQ ID NO: 6).

According to some embodiments, the heavy-chain CDR2 comprises the sequence AVYPGNSDSNYNQKFKA (SEQ ID NO: 41) or AVYPGNSDSNYNQKFQG (SEQ ID NO: 42). According to certain embodiments, the light-chain CDR1 comprises a sequence selected from the group consisting of KASQNVGINVV (SEQ ID NO: 43), KASQNVGINVA (SEQ ID NO: 44), RASQNVGINVV (SEQ ID NO: 45) and RASQNVGINVA (SEQ ID NO: 46).

According to some embodiments, the humanized antibody or a fragment thereof comprises a set of six CDR sequences set forth in SEQ ID NOs: 1, 2, 3, 4, 5, and 6. According to additional exemplary embodiments, the humanized antibody or a fragment thereof comprises a set of six CDR sequences set forth in SEQ ID NOs: 7, 8, 9, 10, (SAS), and 6. According to additional embodiments, the humanized antibody or a fragment thereof comprises a set of six CDR sequences set forth in SEQ ID NOs: 1, 41, 3, 43, 5, and 6.

According to some embodiments, the humanized antibody or antigen binding fragment thereof comprises a heavy chain variable region, comprising:
  i. a set of three CDR sequences comprising the sequences set forth in SEQ ID NOs: 1-3; and
  ii. a set of four heavy chain framework (FR) sequences, wherein FR-H1 is selected from the group consisting of SEQ ID NOs: 21, 25, and 27; FR-H2 is SEQ ID NO: 22; FR-H3 is selected from the group consisting of SEQ ID NOs: 23, 26, 28, and 29; and FR-H4 is SEQ ID NO: 24.

According to some embodiments, the humanized antibody or antigen binding fragment thereof comprising a light chain variable region, comprising:
  i. a set of three CDR sequences comprising the sequences set forth in SEQ ID NOs: 4-6; and
  ii. a set of four light chain framework (FR) sequences, wherein FR-L1 is selected from the group consisting of SEQ ID NOs: 30, 34, 37, and 39; FR-L2 is selected from the group consisting of SEQ ID NOs: 31 and 35; FR-L3 is selected from the group consisting of SEQ ID NOs: 32, 36, 38, and 40; and FR-LA is SEQ ID NO: 33.

According to some embodiments, the humanized antibody or antigen binding fragment thereof comprising a heavy chain variable region and a light chain variable region, the heavy chain variable region comprising:
  i. a set of three CDR sequences comprising the sequences set forth in SEQ ID NOs: 1-3; and
  ii. a set of four heavy chain framework sequences, wherein FR-H1 is selected from the group consisting of SEQ ID NOs: 21, 25, and 27; FR-H2 is SEQ ID NO: 22; FR-H3 is selected from the group consisting of SEQ ID NOs: 23, 26, 28, and 29; FR-H4 is SEQ ID NO: 24;

and the light chain variable region comprising:

i. a set of three CDR sequences comprising the sequences set forth in SEQ ID NOs: 4-6; and ii. a set of four light chain framework sequences, wherein FR-L1 is selected from the group consisting of SEQ ID NOs: 30, 34, 37, and 39; FR-L2 is selected from the group consisting of SEQ ID NOs: 31 and 35; FR-L3 is selected from the group consisting of SEQ ID NOs: 32, 36, 38, and 40; and FR-LA is SEQ ID NO: 33.

According to some embodiments, the humanized antibody or antigen binding fragment thereof comprising a heavy chain variable region and a light chain variable region, the heavy chain variable region comprising:

i. a set of three CDR sequences comprising the sequences set forth in SEQ ID NOs: 7-9; and ii. a set of four heavy chain framework sequences, wherein: FR-H1 is selected from the group consisting of SEQ ID NOs: 21, 25, and 27; FR-H2 is SEQ ID NO: 22; FR-H3 is selected from the group consisting of SEQ ID NOs: 23, 26, 28, and 29; FR-H4 is SEQ ID NO: 24;

and the light chain variable region comprising:

i. a set of three CDR sequences comprising the sequences set forth in SEQ ID NO: 10, the sequence SAS, and SEQ ID NO: 6; and ii. a set of four light chain framework sequences, wherein: FR-L1 is selected from the group consisting of SEQ ID NOs: 30, 34, 37, and 39; FR-L2 is selected from the group consisting of SEQ ID NOs: 31 and 35; FR-L3 is selected from the group consisting of SEQ ID NOs: 32, 36, 38, and 40; and FR-LA is SEQ ID NO: 33.

According to some embodiments, the heavy chain variable region of the humanized monoclonal antibody comprises an amino acid sequence at least about 95% identical to a sequence selected from the group consisting of SEQ ID NO: 11, SEQ ID NO: 13, SEQ ID NO: 14, SEQ ID NO: 15 and SEQ ID NO: 16; and the light chain variable region comprises an amino acid sequence at least about 95% identical to a sequence selected from the group consisting of SEQ ID NO: 12, SEQ ID NO: 17, SEQ ID NO: 18, SEQ ID NO: 19, and SEQ ID NO: 20. In certain embodiments, the heavy chain variable region of the humanized monoclonal antibody comprises an amino acid sequence at least about 97% identical to a sequence selected from the group consisting of SEQ ID NO: 11, SEQ ID NO: 13, SEQ ID NO: 14, SEQ ID NO: 15 and SEQ ID NO: 16; and the light chain variable region comprises an amino acid sequence at least about 97% identical to a sequence selected from the group consisting of SEQ ID NO: 12, SEQ ID NO: 17, SEQ ID NO: 18, SEQ ID NO: 19, and SEQ ID NO: 20. In certain embodiments, the heavy chain variable region of the humanized monoclonal antibody comprises an amino acid sequence selected from the group consisting of SEQ ID NO: 11, SEQ ID NO: 13, SEQ ID NO: 14, SEQ ID NO: 15 and SEQ ID NO: 16, and the light chain variable region comprises an amino acid sequence selected from the group consisting of SEQ ID NO: 12, SEQ ID NO: 17, SEQ ID NO: 18, SEQ ID NO: 19, and SEQ ID NO: 20.

According to some embodiments, the humanized antibody or fragment thereof is a monoclonal antibody, Fab, F(ab) 2, a single-domain antibody, or a single chain variable fragment (scFv).

According to some embodiments, the humanized antibody or fragment thereof is an IgG monoclonal antibody. According to some embodiments, the humanized monoclonal antibody comprises a heavy chain constant region selected from IgG4, IgG1, and IgG2. In certain embodiments, the humanized antibody or fragment thereof is an IgG4 subclass. In certain embodiments, the humanized antibody or antigen binding fragment thereof is an IgG1 sub-class.

According to some embodiments, the humanized monoclonal antibody comprises a kappa light chain constant region.

According to some embodiments, the humanized monoclonal antibody is IgG1, having a heavy chain comprising an amino acid sequence at least about 90%, 95%, or 98% identical to the sequence set forth in SEQ ID NO: 47. According to certain exemplary embodiments, the humanized monoclonal antibody is IgG1, having a heavy chain comprising the amino acid sequence set forth in SEQ ID NO: 47.

According to some embodiments, the humanized monoclonal antibody has a kappa light chain comprising an amino acid sequence at least about 90%, 95%, or 98% identical to the sequence set forth in SEQ ID NO: 49. According to certain exemplary embodiments, the humanized monoclonal antibody has a kappa light chain comprising the amino acid sequence set forth in SEQ ID NO: 49.

According to some embodiments, the humanized antibody has a mutated Fc domain that prevents FcγR-mediated internalization.

According to some embodiments, the humanized antibody comprises a Fc null domain. According to certain embodiments, the Fc domain is null for binding to Fcγ receptors found on immune cells. According to certain exemplary embodiments, the Fc domain is null for binding to CD64, CD32a, CD32b, CD16a, and/or CD16b.

According to some embodiments, the humanized antibody comprises a IgG1 Fc domain. According to certain embodiments, the IgG1 Fc domain is null for binding to Fcγ receptors. According to additional embodiments, the IgG1 Fc domain is null for binding to one or more Fcγ receptors. According to certain exemplary embodiments, the IgG1 Fc domain is null for binding to CD64, CD32a, CD32b, CD16a, and/or CD16b.

According to some embodiments, the humanized antibody comprises a human IgG selected from the group consisting of: (i) a human IgG1 having the mutation L235S; (ii) a human IgG1 having the mutations L235S and E272K; (iii) a human IgG1 having the mutation G237I; (iv) a human IgG1 having the mutations G237I and E272I; (v) a human IgG1 having the mutations G237I and V264R; (vi) a human IgG1 having the mutations V215A, E269R and K322A; (vii) a human IgG1 having the mutations L234A, L235A and P329G; (viii) a human IgG4 having the mutations S228P, L235P and V264R; (ix) a human IgG2 having the mutation P238H; or (x) a human IgG2 having the mutations P238H and V264R. Each possibility represents a separate embodiment of the invention.

According to some embodiments, the humanized antibody comprises a heavy chain sequence selected from the group consisting of SEQ ID NOs: 61-70. Each possibility represents a separate embodiment of the invention.

According to some embodiments, a conjugate comprising the humanized antibody or fragment thereof described above is provided.

Antibodies or fragments thereof according to the present invention are attached, according to some embodiments, to a cytotoxic moiety, a radioactive moiety, or an affinity or labeling tag.

Antibody-drug conjugates (ADCs) according to the present invention comprises the humanized antibodies as described herein, an optional linker, and a toxin.

According to some embodiments, the humanized antibody or fragment thereof is conjugated directly or through a linker, to a toxin (payload).

According to some embodiments, the toxin is selected from the group consisting of microtubule inhibitor, DNA synthesis inhibitor, topoisomerase inhibitor and RNA polymerase inhibitor.

According to certain embodiments, the toxin is a microtubule-destroying drug. According to certain exemplary embodiments, the toxin is auristatin or a derivative thereof. According to certain embodiments, the auristatin derivative is monomethyl auristatin E (MMAE) or monomethyl auristatin F (MMAF).

According to some embodiments, the toxin is saporin.

According to some embodiments, the toxin is a maytansine derivative. According to certain embodiments, the maytansine derivative is DM4 or DM1.

According to some embodiments, the toxin is quinoline alkaloid. According to certain embodiments, the quinoline alkaloid is SN-38.

According to some embodiments, the toxin is a DNA topoisomerase I (TOP1) inhibitor. According to some embodiments, DNA topoisomerase I (TOP1) inhibitor is Exatecan or Exatecan derivative According to certain embodiments, the DNA topoisomerase I (TOP1) inhibitor is DXd.

According to some embodiments, the toxin is directly connected to the antibody. According to other embodiments, the antibody and the toxin are connected through a linker or a spacer. According to some embodiments, the toxin is covalently connected to the humanized antibody directly or through a linker or a spacer. Each possibility represents a separate embodiment of the invention.

According to some embodiments, the linker is cleavable. According to other embodiments, the linker is not cleavable. According to some embodiments, the linker is an enzymatic cleavable linker. According to certain embodiments, the linker is a pH-sensitive linker. According to some embodiments, the linker is a reducible linker (sulfo-SPDB).

According to some embodiments, the linker is selected from the group consisting of Maleimidocaproyl (MC), Maleimidocaproyl-Valine-Citrulline-p-amino-benzyloxy-carbonyl (MC-VC-PAB), Maleimidomethyl cyclohexane-1-carboxylate (SMCC), N-succinimidyl-4-(2-pyridyldithio) butanoate (SPDB) and Lys-PAB-CO (Lysine-p-aminobenzyl-C=O). Each possibility represents a separate embodiment of the invention.

According to some embodiments, polynucleotide sequences encoding the amino acid sequences of heavy chain variable region and light chain variable region described above are provided.

According to some embodiments, the polynucleotide sequence encodes a humanized antibody heavy chain variable region, the polynucleotide comprise a sequence selected from the group consisting of SEQ ID NOs: 51-55 or a variant thereof having at least 80% sequence identity. Each possibility represents a separate embodiment of the invention.

According to some embodiments, the polynucleotide sequence encodes a humanized antibody light chain variable region, the polynucleotide comprise a sequence selected from the group consisting of SEQ ID NOs: 56-60 or a variant thereof having at least 80% sequence identity. Each possibility represents a separate embodiment of the invention.

According to some embodiments, the polynucleotide sequence encodes a humanized antibody heavy chain variable region, the polynucleotide comprise a sequence selected from the group consisting of SEQ ID NOs: 51-55. According to some embodiments, the polynucleotide sequence encodes a humanized antibody light chain variable region, the polynucleotide comprise a sequence selected from the group consisting of SEQ ID NOs: 56-60.

According to some embodiments, the polynucleotide sequence encodes a humanized antibody heavy chain variable region, said polynucleotide comprise a sequence set forth in SEQ ID NO: 51. According to some embodiments, said polynucleotide sequence encodes a humanized antibody light chain variable region, the polynucleotide comprise a sequence set forth in SEQ ID NO: 56.

According to some embodiments, polynucleotide sequences encoding the amino acid sequences of humanized antibody heavy chain and light chain described above are provided.

According to some embodiments, the polynucleotide sequence encoding the humanized antibody heavy chain comprises a sequence set forth in SEQ ID NO: 48 or a variant thereof having at least 80% sequence identity. According to some embodiments, the polynucleotide sequence encoding the humanized antibody light chain comprises a sequence set forth in SEQ ID NO: 50 or a variant thereof having at least 80% sequence identity.

According to some embodiments, the DNA sequence encoding the amino acid chain of a humanized antibody as described herein comprises a leader sequence. According to certain exemplary embodiments, the DNA sequence encodes a leader peptide sequence set forth in SEQ ID NO: 71.

In a further aspect, the present invention provides a nucleic acid construct comprising a nucleic acid molecule encoding at least one humanized antibody chain or fragment thereof as described herein. According to some embodiments the nucleic acid construct is a plasmid.

Also described is a cell line comprising the nucleic acids encoding the antibodies of the present invention. The cell line is for expression of the humanized antibody or fragment thereof as described herein. In certain embodiments, the cell line is a mammalian cell line such as a Chinese Hamster Ovary (CHO) cell line.

The present invention provides, according to another aspect, a pharmaceutical composition comprising the humanized antibody or antigen binding fragment described herein or a conjugate comprising the antibody and a pharmaceutically acceptable excipient, carrier, or diluent.

According to some embodiments, the pharmaceutical composition is for use in treating cancer.

Any administration mode may be used to deliver the compositions of the present invention to a subject in need thereof, including parenteral and enteral administration modes.

According to some embodiments, the pharmaceutical composition is formulated for injection or infusion. According to some embodiments, the pharmaceutical composition is formulated for intravenous administration. In certain embodiments, the pharmaceutical composition is formulated for intratumoral administration.

According to yet another aspect, the present invention provides a method of treating cancer comprising administering to a subject in need thereof, a therapeutically effective amount of at least one humanized antibody or its conjugate as described herein.

According to some embodiments, the cancer is characterized by overexpression of Nectin-2.

In certain embodiments, the cancer comprises a solid tumor.

In certain embodiments, the cancer is selected from the group consisting of prostate cancer, colorectal cancer, liver cancer, ovarian cancer, endometrial cancer, stomach cancer, thyroid cancer, carcinoid tumor, head and neck cancer, breast cancer, pancreatic cancer, testis cancer, urothelial cancer, cervical cancer, melanoma, lymphoma and lung cancer. Each possibility represents a separate embodiment of the invention.

According to some embodiments, the cancer is breast cancer. According to some embodiments, the cancer is colorectal adenocarcinoma or lung adenocarcinoma.

According to other embodiments, the cancer is a hematological cancer. According to some embodiments, the hematological cancer is selected from leukemia including acute myeloid leukemia (AML), chronic myeloid leukemia (CML), acute lymphocytic leukemia (ALL), and chronic lymphocytic leukemia (CLL); lymphoma, including Hodgkin disease, and non-Hodgkin lymphoma; and multiple myeloma.

According to some embodiments, the subject is human.

According to some embodiments, the method of treating cancer comprises administering or performing at least one additional anti-cancer therapy. According to certain embodiments, the additional anticancer therapy is surgery, chemotherapy, radiotherapy, or immunotherapy.

According to some embodiments, the method of treating cancer comprises administration of the humanized antibody described herein and an additional anti-cancer agent. According to some embodiments, the additional anti-cancer agent is selected from the group consisting of: immune-modulator, activated lymphocyte cell, kinase inhibitor and chemotherapeutic agent.

According to other embodiments, the additional immune-modulator is an antibody, antibody fragment or antibody conjugate that binds to an antigen other than human Nectin-2.

According to some embodiments, the additional immune-modulator is an antibody against an immune checkpoint molecule. According to some embodiments, the additional immune modulator is an antibody against an immune checkpoint molecule selected from the group consisting of human programmed cell death protein 1 (PD-1), PD-L1 and PD-L2, carcinoembryonic antigen-related cell adhesion molecule 1 (CEACAM1), lymphocyte activation gene 3 (LAG3), CD137, OX40 (also referred to as CD134), killer cell immunoglobulin-like receptors (KIR), TIGIT, PVR, CTLA-4, NKG2A, GITR, and any other checkpoint molecule or a combination thereof. Each possibility represents a separate embodiment of the invention. According to certain embodiments, the additional immune modulator is an antibody against PD-1. According to some embodiments, the additional immune modulator is an antibody against CTLA-4.

According to some embodiments, the anti-cancer agent is selected from the group consisting of: erbitux, cytarabine, fludarabine, fluorouracil, mercaptopurine, methotrexate, thioguanine, gemcitabine, vincristine, vinblastine, vinorelbine, carmustine, lomustine, chlorambucil, cyclophosphamide, cisplatin, carboplatin, ifosfamide, mechlorethamine, melphalan, thiotepa, dacarbazine, bleomycin, dactinomycin, daunorubicin, doxorubicin, idarubicin, mitomycin, mitoxantrone, plicamycin, etoposide, teniposide and any combination thereof. Each possibility represents a separate embodiment of the invention.

According to some embodiments, the method of treating cancer involves preventing or reducing formation, growth or spread of metastases in a subject.

According to an additional aspect, the present invention provides an antibody-drug conjugates comprising a humanized antibody that specifically binds human Nectin-2 and a toxin, for use in treating cancer.

The cancer and the toxin are as described above.

According to some embodiments, the humanized antibody comprises a mutated Fc domain.

The present invention further provides, according to an aspect, a method of diagnosing or prognosing cancer in a subject, the method comprises determining the expression level of Nectin-2 in a biological sample of said subject using at least one humanized antibody, fragment or conjugate as described herein.

The present invention further provides, according to another aspect, a method of determining or quantifying the expression of Nectin-2, the method comprising contacting a biological sample with an antibody or antibody fragment as described herein, and measuring the level of complex formation.

According to some embodiments, the method for detecting or quantifying the expression of Nectin-2 comprises the steps of:

i. incubating a sample with the antibody specific to Nectin-2 or an antibody fragment thereof comprising at least an antigen-binding portion;

ii. detecting the bound Nectin-2 using a detectable probe.

According to some embodiments, the method further comprises the steps of:

iii. comparing the amount of (ii) to a standard curve obtained from a reference sample containing a known amount of Nectin-2; and iv. calculating the amount of the Nectin-2 in the sample from the standard curve.

According to some particular embodiments, the sample is a body fluid or solid tissue. In some embodiments, the method is performed in-vitro or ex-vivo.

A kit for measuring the expression of Nectin-2 in biological sample is also provided comprising at least one antibody or antibody fragment as described herein and means for measuring Nectin-2 expression. In some embodiment, the kit further comprising instruction material directing the use of the kit.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

(also termed CD226) is an activating receptor on many immune cells (e.g., T cells), and CD112R (also termed PVRIG) and TIGIT are co-inhibitory receptors on lymphoid immune cells (e.g., T and NK cells); Nectin-2 acts as an inhibitory ligand for immune cells, mainly via its high-affinity binding to CD112R (rectangle).

Figure 3:
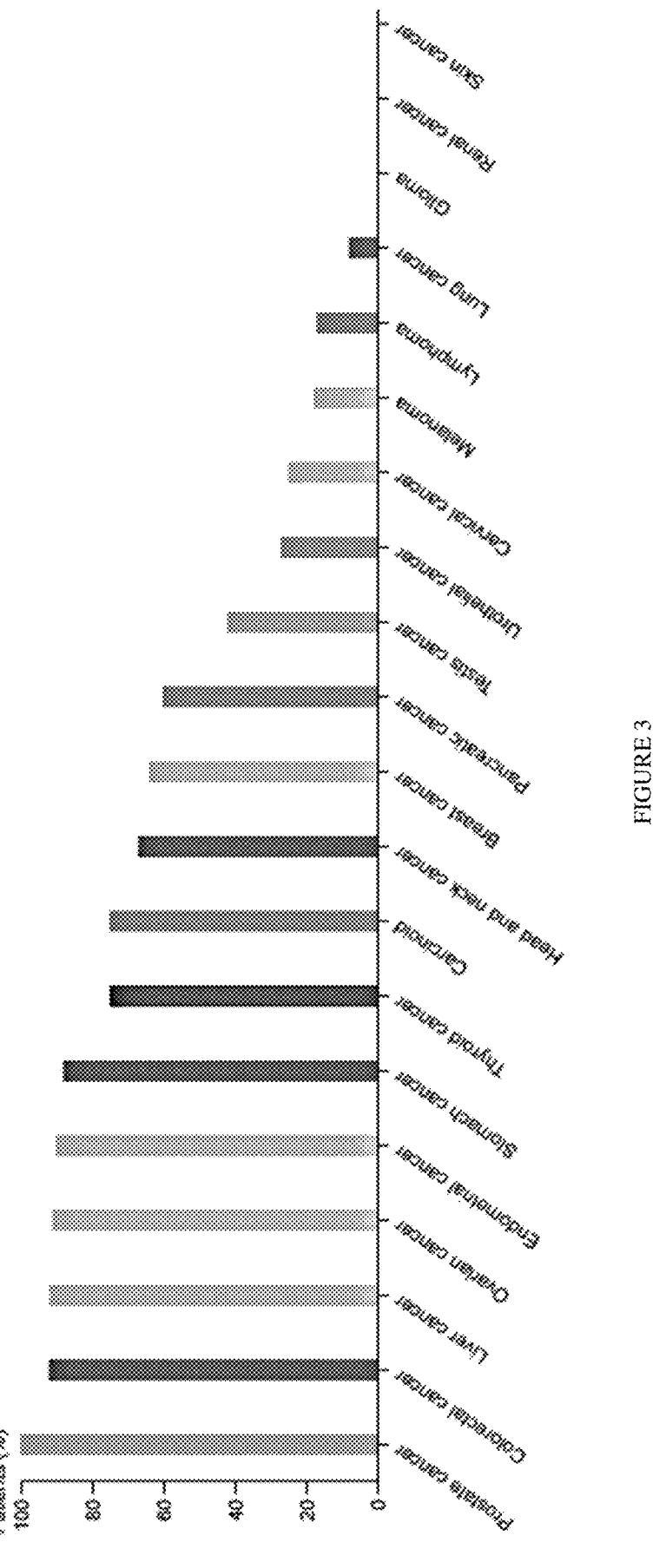

FIG. 3 is a graph showing percent of tumors positive for Nectin-2 expression. Data obtained from proteinatlas.com using the HPA012759 mAb (anti Nectin-2; Sigma-Aldrich®). In 17/20 indications moderate-high membranous expression of Nectin-2 is seen.

Figure 4B:
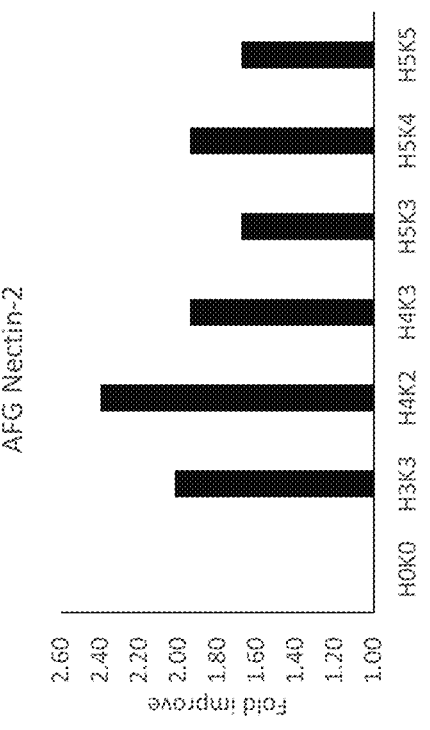
Figure 4A:
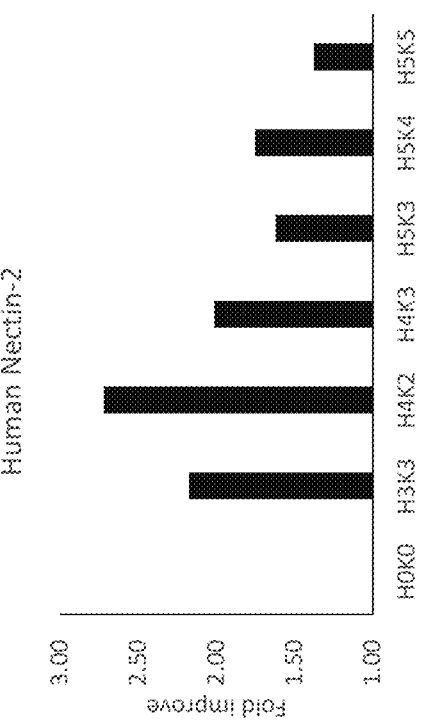
Figure 4C:
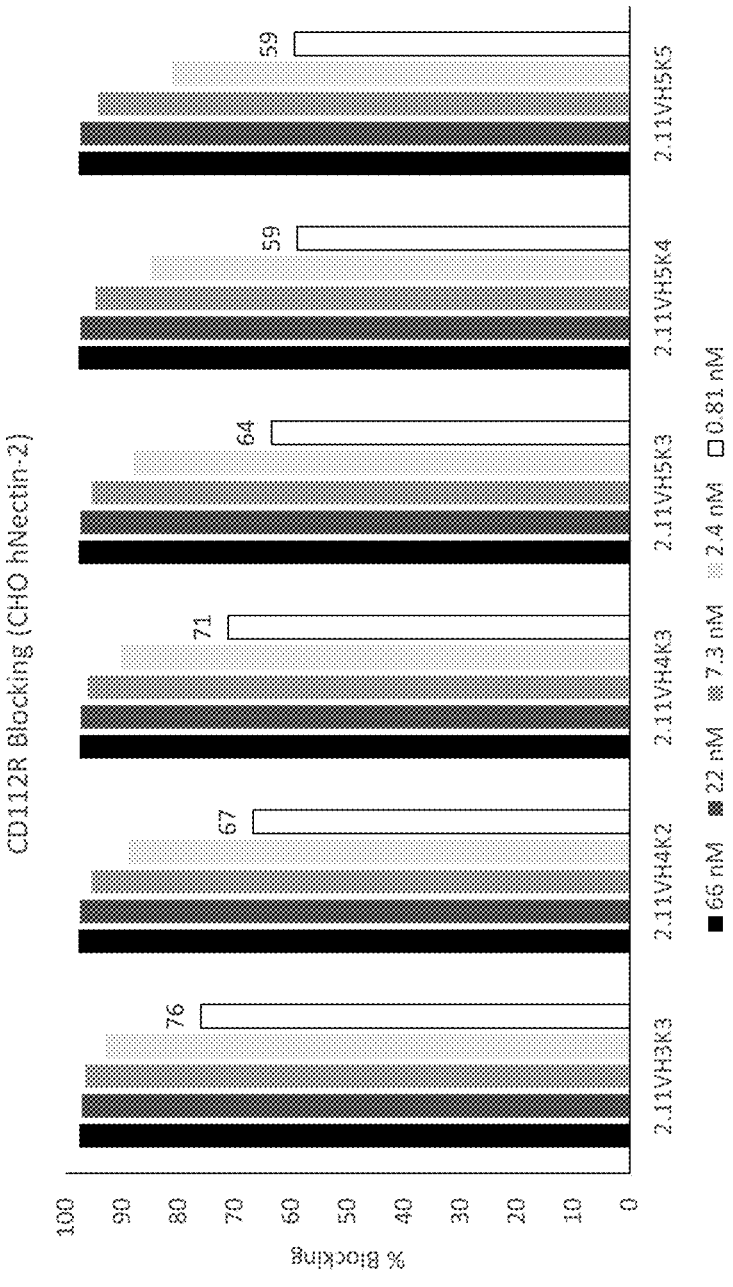

FIGS. 4A-4C depict improved on-cell binding of the humanized variants of the parental (chimeric) anti-Nectin2 mAb. Nectin-2 expressing cells were analyzed by FACS analysis for binding of serially diluted mAb humanized variants. EC-50 values were calculated for each variant and are reported relative to the EC-50 value of the chimeric Ab (HOKO), which was set as 1. FIG. 4A-fold change EC-50 binding to 293T cells expressing human Nectin-2. FIG. 4B-fold change EC-50 binding to Vero cells derived from African green monkey (AFG, Chlorocebus) and naturally expressing Nectin-2 (XP_007995342.1). FIG. 4C-results of CD112R blocking by the different humanized mAb variants, as assessed by FACS analysis of CD112R-Fc binding to CHO(K)1 cells overexpressing human Nectin-2, in presence of the anti-Nectin-2 humanized clones in concentrations from 66-0.81 nM. Variants maintaining >70% blocking capacity at the lowest dose were considered superior.

Figure 5B:
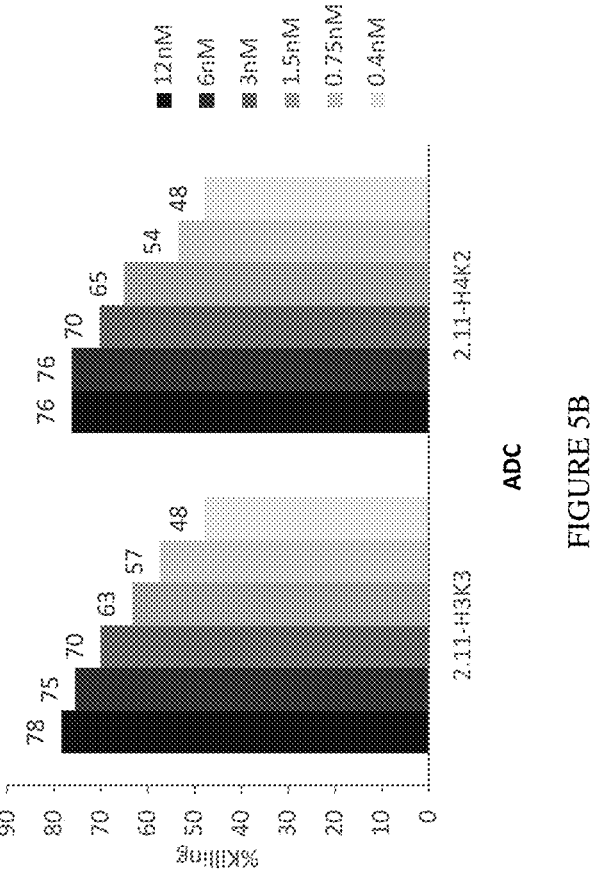
Figure 5A:
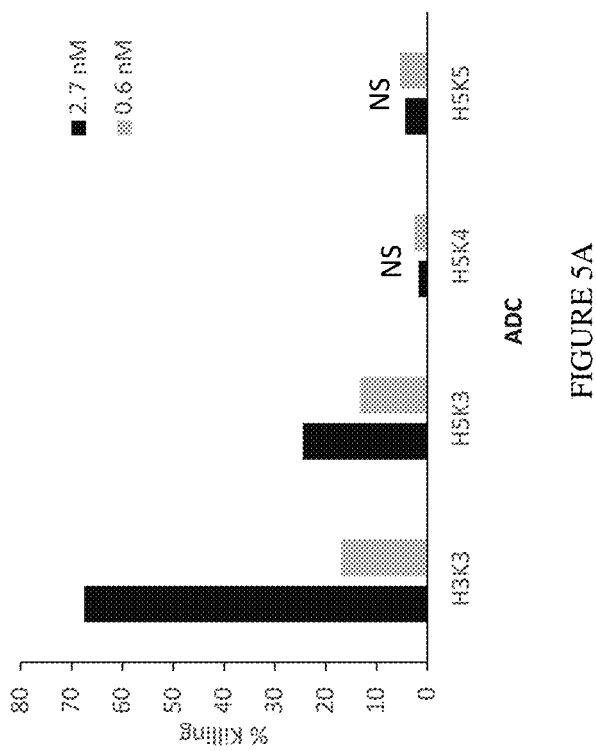
Figure 5C:
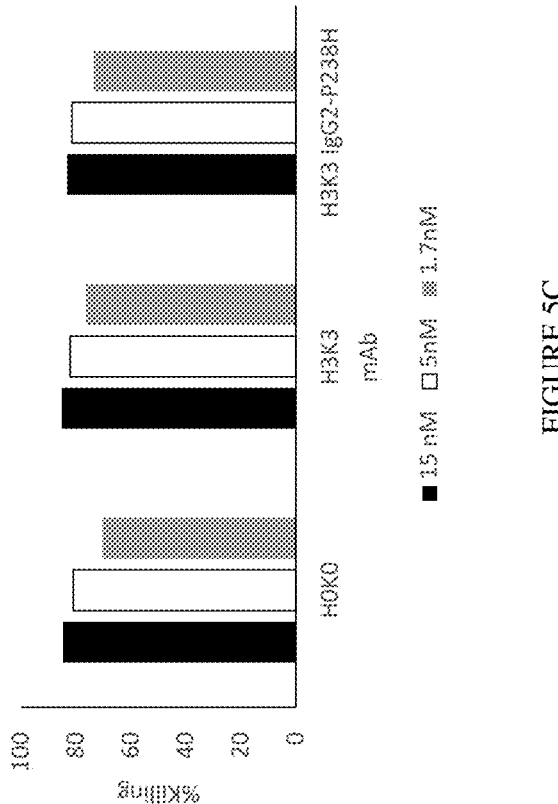

FIGS. 5A-5C depict the killing effect of humanized anti-Nectin-2 ADC variants. ADC was based on Saporin (ZAP) and the A549 target cells (lung adenocarcinoma) were confirmed to express Nectin-2. FIG. 5A shows the superior killing effect of the lead clone H3K3, compared to other humanized variants tested at two concentrations. FIG. 5B depicts comparable levels of ADC activity between the humanized H3K3 and H4K2 variants. FIG. 5C-comparable levels of ADC activity between the chimeric mAb (HOKO), and the humanized H3K3 variant at three concentrations. H3K3 was also tested when grafted on IgG2-P238H, which has an FcgR-null Fc, and which had no effect on the potency of this variant. All killing results are significant (p<0.001, two-way t-test), unless indicated by NS (not significant).

Figure 6B:
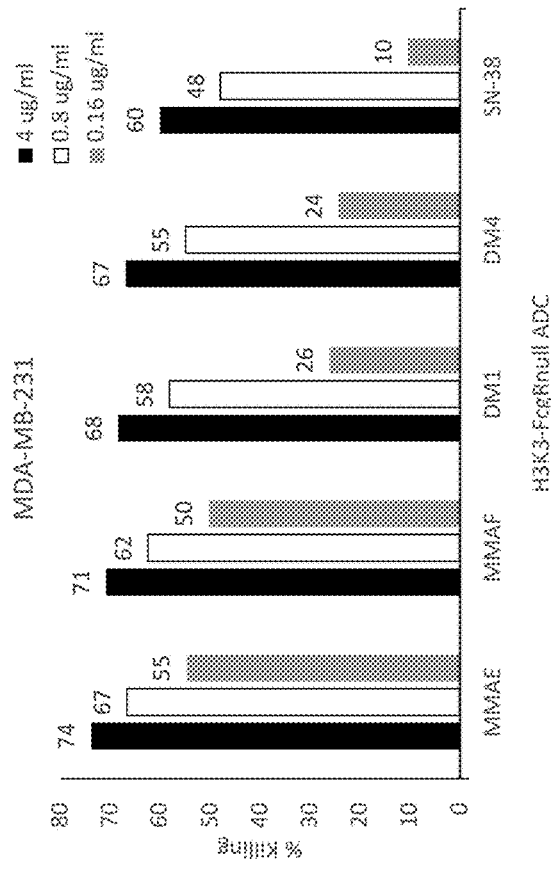
Figure 6A:
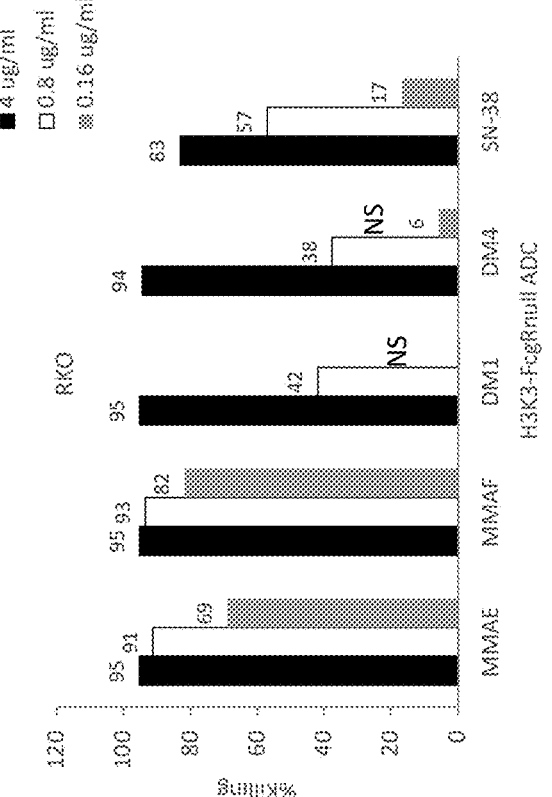
Figure 6C:
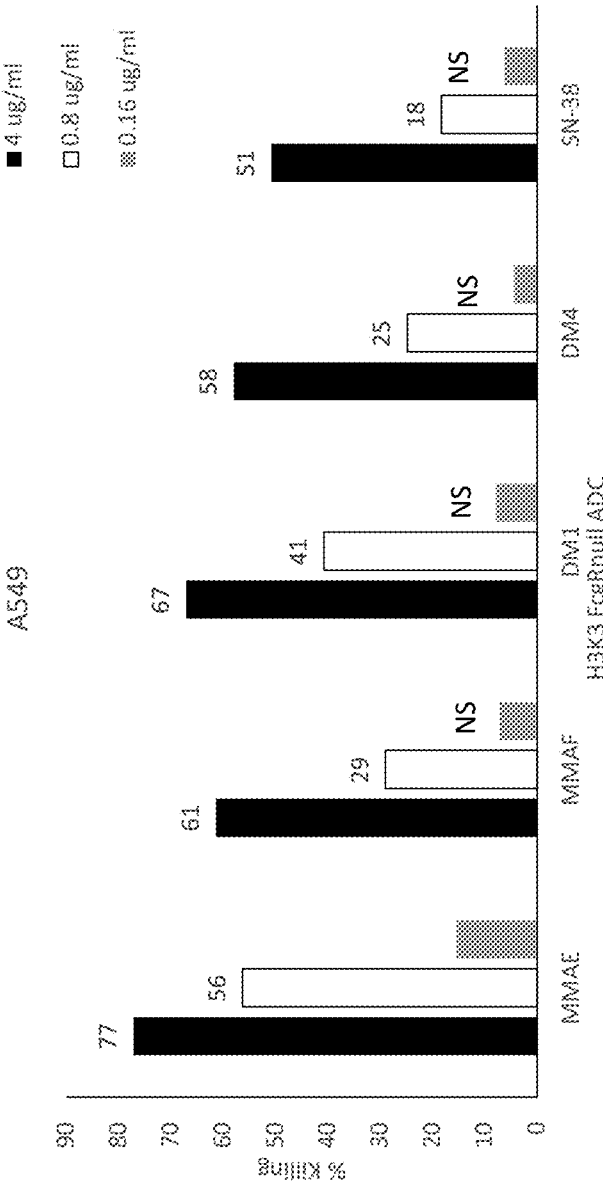

FIGS. 6A-6C demonstrate that humanized H3K3-FcgR$^{null}$ anti-Nectin-2 ADCs, conjugated to various toxins, lead to robust killing of various solid tumor cell lines. The Figures show significant killing activity of the H3K3-FcgR$^{null}$ ADCs, at different ADC concentrations and across different cancer targets after 72 hours of incubation. FIG. 6A depicts killing of RKO cells (colorectal adenocarcinoma). FIG. 6B depicts killing of MDA-MB-231 cells (triple negative breast cancer). FIG. 6C depicts killing of A549 cells (lung adenocarcinoma). Killing of target cells was significant (p<0.001), unless indicated by NS (not significant). While all ADCs had a toxic effect, its magnitude varied pending the conjugated toxin and nature of target cells. Still, the ADCs containing either MMAE or MMAF were superior to all others across all target cells.

Figure 7:
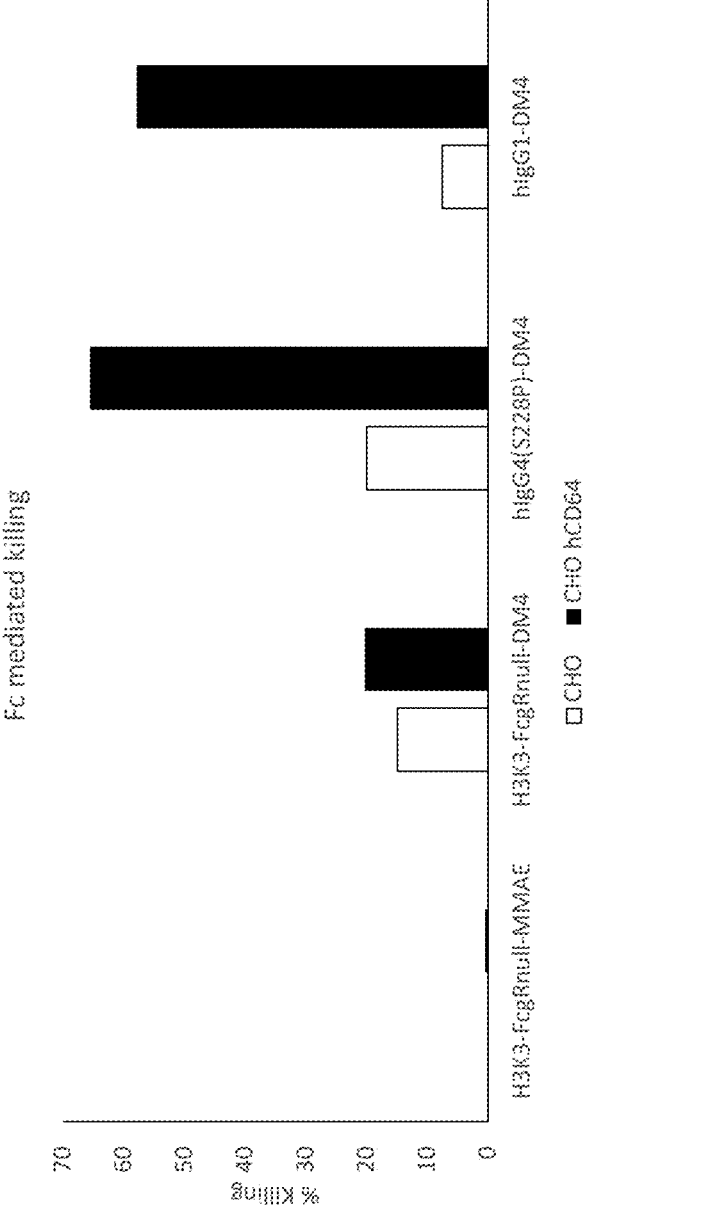

FIG. 7 demonstrates that humanized H3K3-FcgR$^{null}$ anti-Nectin-2 ADCs are not internalized via interaction with the high affinity FcgR-CD64. CHO-K1 cells or CHO-K1 cells overexpressing human CD64 (hCD64), but not Nectin-2, were incubated with two versions of H3K3-FcgR$^{null}$ ADCs (conjugated to either MMAE or DM4), or with control irrelevant ADCs that have either hIgG4 (S228P) or hIgG1 Fc (both conjugated to DM4), at 12 ug/ml for 72 hours. Specific increased killing was seen for the CD64 positive cells when either hIgG4 or hIgG1 was used, but not when the FogRnull Fc H3K3 ADC variants were used. Note that background, non-specific killing was induced by DM4, regardless of either Nectin-2 or CD64 expression by the target cells.

Figure 8:
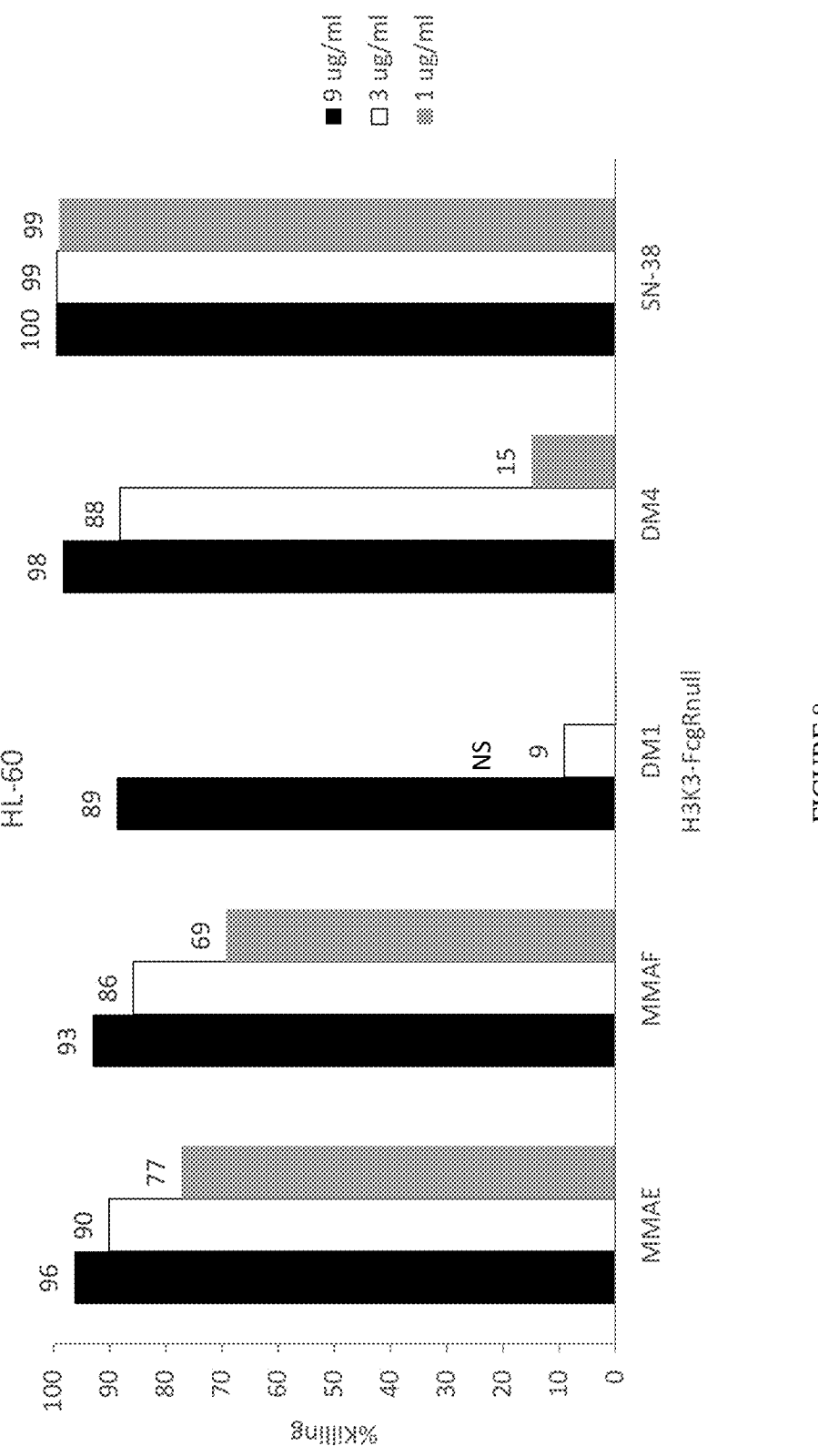

FIG. 8 demonstrates that humanized H3K3-FcgR$^{null}$ anti-Nectin-2 ADCs lead to robust killing of a hematological cell line. H3K3-FcgR$^{null}$ Abs, with the indicated linker-payload combinations, were incubated at concentration from 9-1 mg/ml, for 72 hours with HL-60 cells (an AML model). All linker-payload combinations, except DM1, resulted in >90% killing at the high dose and significant killing at all doses tested (p<0.001).

Figures 9A, 9B:
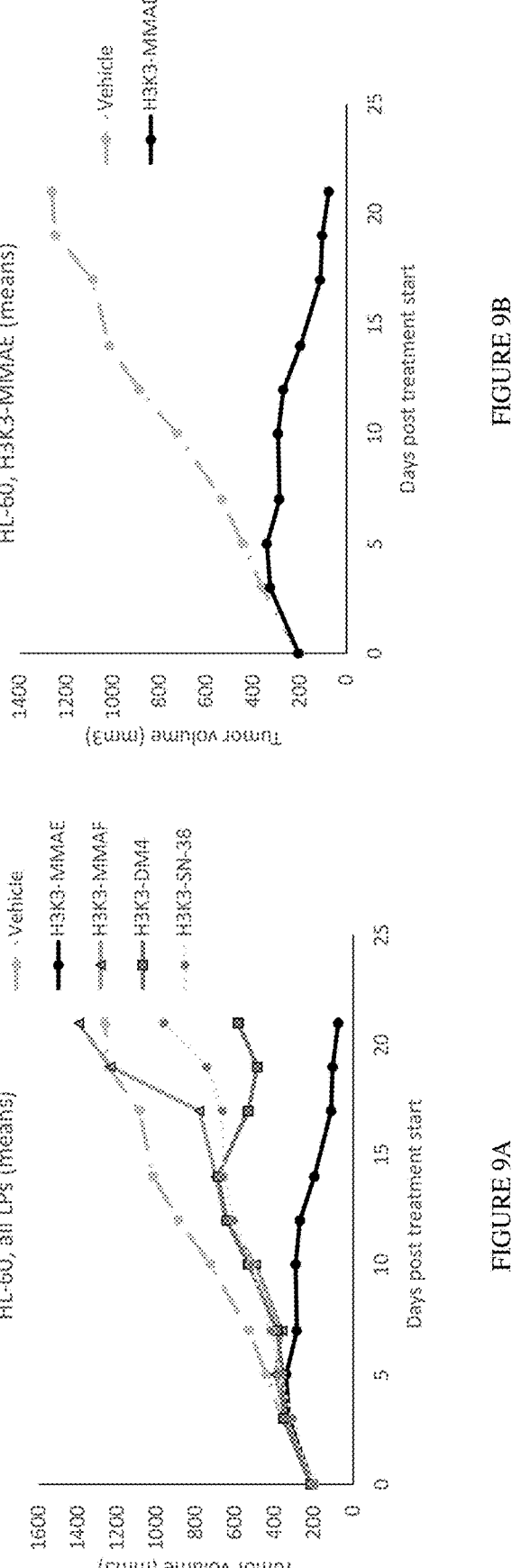

FIGS. 9A-9B depict in-vivo efficacy of the humanized H3K3-FcgR$^{null}$ anti-Nectin-2 ADCs against the hematological tumor cells line, HL-60 implanted s.c. to Nude female mice. FIG. 9A compares the effect of treatment with different combinations of linker payloads (LP). Two of the LP combinations had a significant effect: DM4 resulted in significant tumor growth inhibition (TGI, p<0.05), while complete tumor regression was seen for MMAE. The effect of the MMAE-based ADC is shown in FIG. 9B without including the other treatments.

Figure 10:
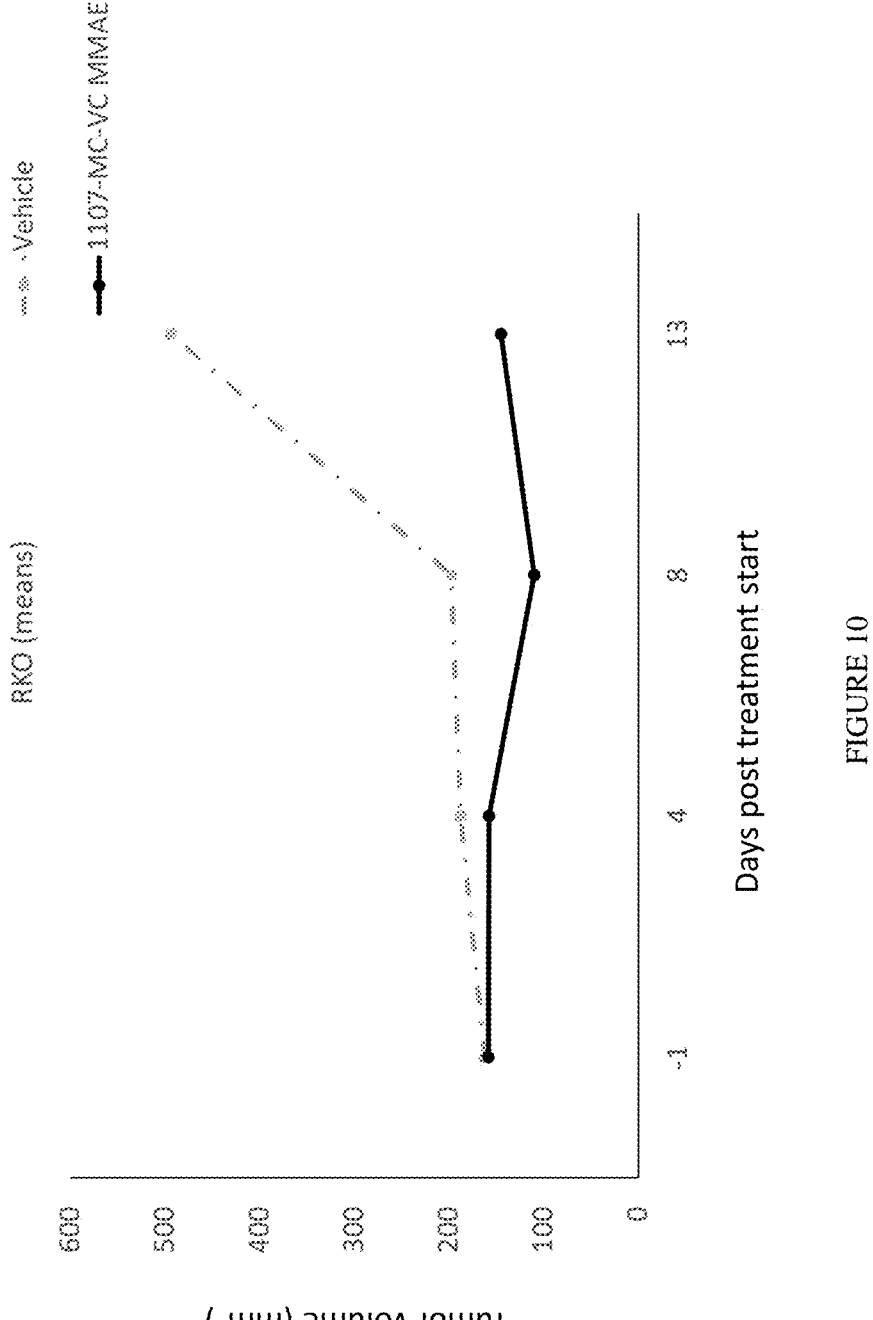

FIG. 10 depicts in-vivo efficacy of the humanized H3K3-FcgR$^{null}$ anti-Nectin-2 ADC (1107-MC-VC-MMAE) against the solid (colorectal adenocarcinoma) tumor cell line, RKO. An empty vehicle was used as control.

Figure 11:
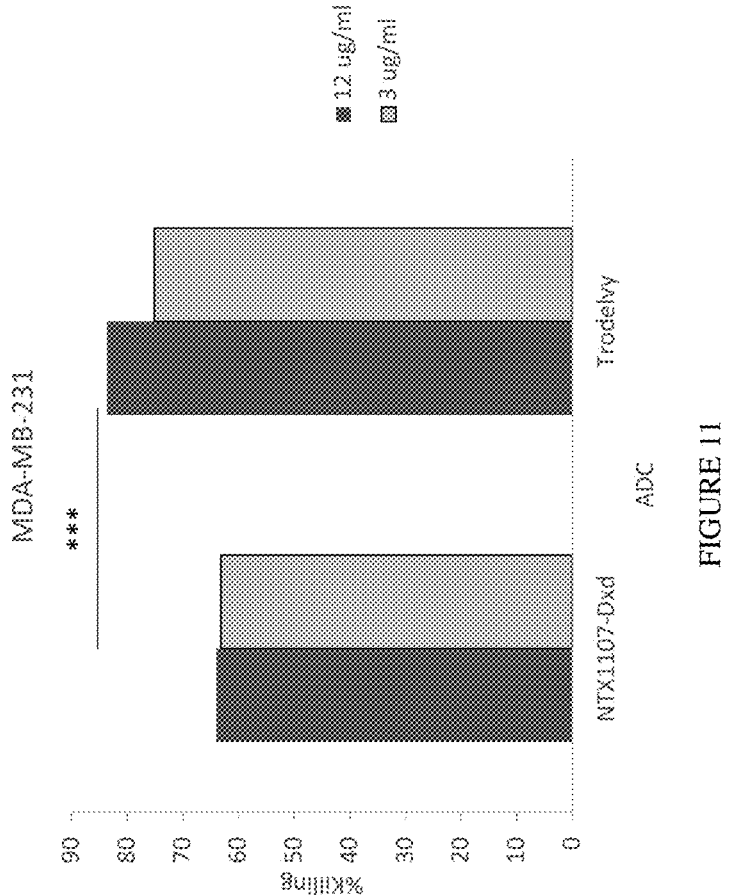

FIG. 11 depicts in-vitro killing of MDA-MB-231 (triple negative breast cancer or TNBC) cells by the humanized H3K3-FcgR$^{null}$ anti-Nectin-2 mAb (NTX1107) linked to Dxd, compared to Trodelvy (Sacituzumab govitecan), an approved ADC drug for TNBC. Both ADCs use the same class of cytotoxic payload (i.e., topoisomerase I (TOP1) inhibitors). MDA-MB-231 cells were incubated in presence of the indicated concentration of these ADCs. Killing was evaluated after 120 hours. Robust killing of target cells was induced by both ADCs with significant superiority of Trodelvy at both concentrations (*** p<0.0005).

Figure 12:
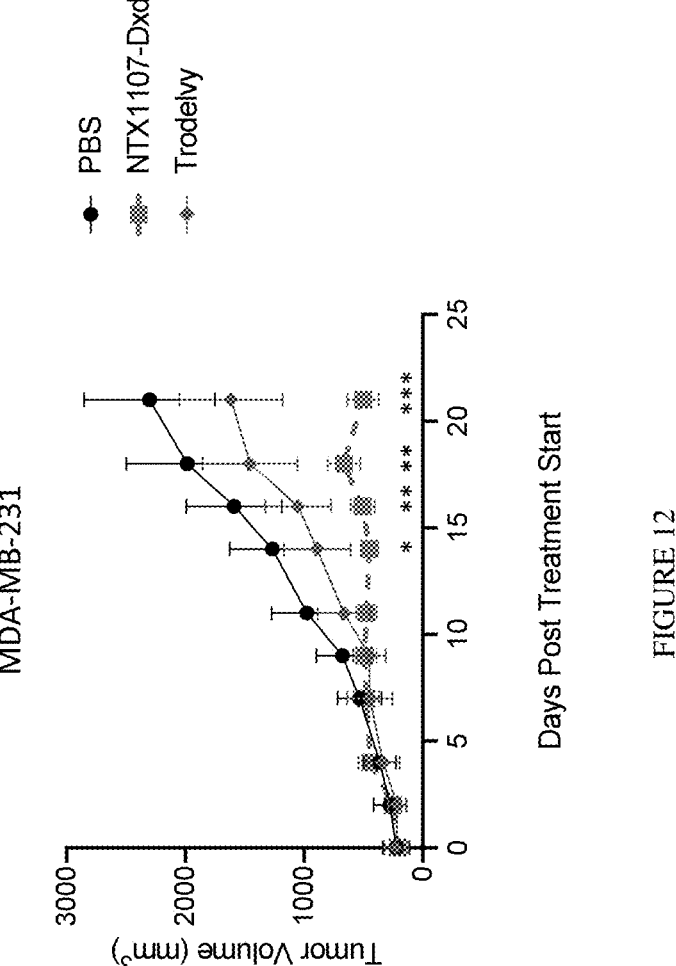

FIG. 12 depicts in-vivo efficacy of humanized H3K3-FcgR$^{null}$ anti-Nectin-2 ADC (NTX1107), compared to Trodelvy, against MDA-MB-231 s.c. tumor model in Nude female mice. NTX1107-Dxd was able to significantly inhibit tumor growth, resulting in tumor stasis, while Trodelvy had no effect on tumor growth at the same treatment regimen.

Figure 13:
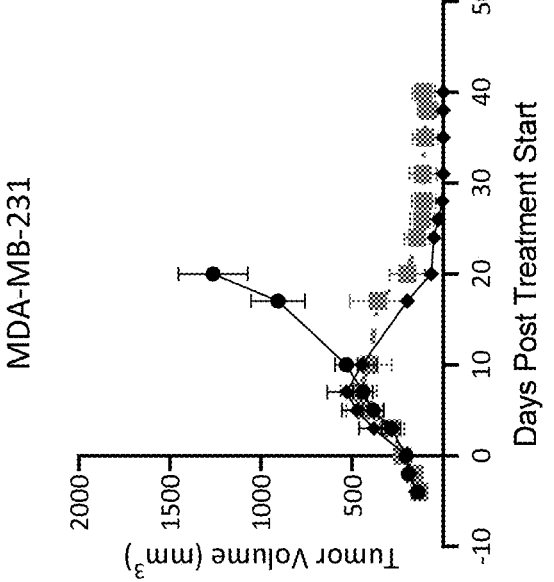

FIG. 13 compares the effect of in-vivo treatment with H3K3-FcgR$^{null}$-Dxd (NTX1107-Dxd) to that of H3K3-FcgR$^{null}$ MMAE (NTX1107-MMAE) against MDA-MB-231 s.c. tumor model in Nude female mice. Complete tumor regression was seen for H NTX1107-MMAE with 7/7 mice having no measurable tumors at the end of the study. Tumor regression was seen for NTX1107-Dxd with 4/7 mice having no measurable tumors at the end of the study.

DETAILED DESCRIPTION OF THE INVENTION

The present invention provides humanized monoclonal antibodies that recognize Nectin-2. Advantageously, the antibodies of the invention are almost fully humanized, thus avoiding the risk of adverse immune response towards the antibodies and are therefore likely to be safe for use in humans. The antibodies of the invention are characterized by having unique CDR sequences and novel humanized framework sequences and design.

The present invention further provides in some embodiments antibody-drug conjugates, or ADCs, comprising the humanized antibodies described herein, which are useful in treating cancer.

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

As used herein the term "about" refers to an amount that is near the stated amount by 10% or less.

The term "Nectin-2" or "Nectin Cell Adhesion Molecule 2", as used herein refers to a human plasma membrane glycoprotein, also known as CD112, and PVRL2. The Nectin-2 protein is a single-pass type I membrane glycoprotein with two Ig-like C2-type domains and an Ig-like V-type domain. This protein is one of the plasma membrane components of adherent junctions. It also serves as an entry for certain mutant strains of herpes simplex virus and pseudorabies virus, and it is involved in cell to cell spreading of these viruses. An exemplary Nectin-2 according to the invention is set forth in SwissPort, UniPort and GenBank symbols or accession numbers: Gene ID: 5819, Q92692, 168093, NP_001036189.1, NP_002847.1, and #Q92692.

According to an aspect, the present invention provides a humanized antibody that specifically bind Nectin-2, or a fragment thereof comprising at least the antigen binding site, wherein the antibody or a fragment thereof comprises a heavy chain and a light chain, wherein the heavy chain comprises a variable region having an amino acid sequence at least about 90% identical to a sequence selected from the group consisting of SEQ ID NO: 11, SEQ ID NO: 13, SEQ ID NO: 14, SEQ ID NO: 15 and SEQ ID NO: 16; and wherein the light chain comprises a variable region having an amino acid sequence at least about 90% identical to a sequence selected from the group consisting of SEQ ID NO: 12, SEQ ID NO: 17, SEQ ID NO: 18, SEQ ID NO: 19 and SEQ ID NO: 20.

According to another aspect, the present invention provides a humanized antibody that specifically binds Nectin-2, or a fragment thereof comprising at least the antigen binding site, wherein the antibody, or a fragment thereof, comprises a heavy chain variable region and a light chain variable region, the heavy chain variable region comprising:

(i) a set of three CDR sequences comprising the sequences set forth in SEQ ID NOs: 1-3; and (ii) a set of four heavy chain framework sequences, wherein: FR-H1 (frame work heavy chain No. 1) is selected from the group consisting of SEQ ID NOs: 21, 25, and 27; FR-H2 is SEQ ID NO: 22; FR-H3 is selected from the group consisting of SEQ ID NOs: 23, 26, 28, and 29; FR-H4 is SEQ ID NO: 24; and the light chain variable region comprising:

(i) a set of three CDR sequences comprising the sequences set forth in SEQ ID NOs: 4-6; and (ii) a set of four light chain framework sequences, wherein FR-L1 (frame work light chain No. 1) is selected from the group consisting of SEQ ID NOs: 30, 34, 37, and 39; FR-L2 is selected from the group consisting of SEQ ID NOs: 31 and 35; FR-L3 is selected from the group consisting of SEQ ID NOs: 32, 36, 38, and 40; and FR-L4 is SEQ ID NO: 33.

The frameworks are the non-CDR sequences of the chain variable regions. FR-H1 is the sequence before CDR1 in the heavy variable chain, FR-H2 is the sequence between CDR1 and CDR2, FR-H3 is the sequence between CDR2 and CDR3, and FR-H4 is the sequence after CDR3. FR-L1 is the sequence before CDR1 in the light variable chain, FR-L2 is the sequence between CDR1 and CDR2, FL-H3 is the sequence between CDR2 and CDR3, and FR-L4 is the sequence after CDR3.

According to an additional aspect, the present invention provides a humanized antibody or antigen binding fragment thereof comprising a heavy chain variable region and a light chain variable region, the heavy chain variable region comprising:

i. a set of three CDR sequences, the CDRs comprising the sequences SYW, SEQ ID NO: 8, and SEQ ID NO: 3; and ii. a set of four heavy chain framework sequences, wherein: FR-H1 is selected from the group consisting of SEQ ID NOs: 21, 25, and 27; FR-H2 is SEQ ID NO: 22; FR-H3 is selected from the group consisting of SEQ ID NOs: 23, 26, 28, and 29; FR-H4 is SEQ ID NO: 24;

and the light chain variable region comprising:

i. a set of three CDR sequences, the CDRs comprising the sequences set forth in SEQ ID NO: 10, SAS, and SEQ ID NO: 6; and ii. a set of four light chain framework sequences, wherein: FR-L1 is selected from the group consisting of SEQ ID NOs: 30, 34, 37, and 39; FR-L2 is selected from the group consisting of SEQ ID NOs: 31 and 35; FR-L3 is selected from the group consisting of SEQ ID NOs: 32, 36, 38, and 40; and FR-L4 is SEQ ID NO: 33.

According to some embodiments, the humanized antibody or fragment thereof comprises a heavy chain variable region comprising a set of three CDR sequences, the CDRs comprising the sequences SEQ ID NO: 7, SEQ ID NO: 8, and SEQ ID NO: 9; and a light chain variable region comprising a set of three CDR sequences, the CDRs comprising the sequences SEQ ID NO: 10, SAS, and SEQ ID NO: 6.

Among the provided antibodies are monoclonal antibodies, polyclonal antibodies, multispecific antibodies (for example, bispecific antibodies and polyreactive antibodies), and antibody fragments. The antibodies include antibody-conjugates and molecules comprising the antibodies, such as chimeric molecules. Thus, an antibody includes, but is not limited to, full-length, as well as fragments and portion thereof retaining the binding specificities thereof, such as any specific binding portion thereof including those having any number of, immunoglobulin classes and/or isotypes (e.g., IgG1, IgG2, IgG3, IgG4, IgM, IgA, IgD, IgE and IgM); and biologically relevant (antigen-binding) fragments or specific binding portions thereof, including but not limited to Fab, F(ab') 2, Fv, and scFv (single chain or related entity). A monoclonal antibody is generally one within a composition of substantially homogeneous antibodies; thus, any individual antibodies comprised within the monoclonal antibody composition are identical except for possible naturally occurring mutations that may be present in minor amounts. A polyclonal antibody is a preparation that includes different antibodies of varying sequences that generally are directed against two or more different determinants (epitopes). The monoclonal antibody can comprise a human IgG1 constant region. The monoclonal antibody can comprise a human IgG4 constant region.

The term "antibody" herein is used in the broadest sense and includes polyclonal and monoclonal antibodies, including intact antibodies and functional (antigen-binding) antibody fragments thereof, including fragment antigen binding (Fab) fragments, F(ab') 2 fragments, Fab' fragments, Fv fragments, recombinant IgG (rIgG) fragments, single chain antibody fragments, including single chain variable fragments (sFv or scFv), and single domain antibodies (e.g., sdAb, sdFv, nanobody) fragments. The term encompasses genetically engineered and/or otherwise modified forms of immunoglobulins, such as intrabodies, peptibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD. The antibody can comprise a human IgG1 constant region. The antibody can comprise a human IgG4 constant region.

CDR identification or determination from a given heavy or light chain variable sequence, is typically made using one of few methods known in the art. For example, such determination is made according to the Kabat (Wu T. T and Kabat E. A., *J Exp Med,* 1970; 132:211-50) and IMGT (Lefranc M-P, et al., *Dev Comp Immunol,* 2003, 27:55-77).

When the term "CDR having a sequence", or a similar term is used, it includes options wherein the CDR comprises the specified sequences and also options wherein the CDR consists of the specified sequence.

The antigen specificity of an antibody is based on the hyper variable region (HVR), namely the unique CDR sequences of both light and heavy chains that together form the antigen-binding site.

Among the provided antibodies are antibody fragments. An "antibody fragment" refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab') 2; diabodies; linear antibodies; single-chain antibody molecules (e.g., scFv or sFv); and multispecific antibodies formed from antibody fragments. In particular embodiments, the antibodies are single-chain antibody fragments comprising a variable heavy chain region and/or a variable light chain region, such as scFvs.

A "humanized" antibody is an antibody in which all or substantially all CDR amino acid residues are derived from non-human CDRs and all or substantially all framework region (FR) amino acid residues are derived from human FRs. A humanized antibody optionally may include at least a portion of an antibody constant region derived from a human antibody. A "humanized form" of a non-human antibody refers to a variant of the non-human antibody that has undergone humanization, typically to reduce immunogenicity to humans, while retaining the specificity and affinity of the parental non-human antibody. According to some embodiments, some FR residues in a humanized antibody are substituted with corresponding residues from a non-human antibody (e.g., the antibody from which the CDR residues are derived), e.g., to restore or improve antibody specificity or affinity.

The amino acid residues in the Fc domain can be substituted to be null, meaning the Fc domain does not bind Fc receptors or can bind with such low affinity and/or avidity as to not cause any Fc receptor signaling as a result of binding. The Fc domain can be null for binding to Fcγ receptors. Some example Fcγ receptors for which the Fc domain can be null for binding can be, but not limited to, FcγRI (CD64), FcγRIIA (CD32a), FcγRIIB (CD32b), FcγRIIIA (CD16a), FcγRIIIA (CD16a) F158 variant, FcγRIIIA (CD16a) V158 variant, or FcγRIIIB (CD16b). The Fc domain may have one or more, two or more, three or more, or four or more amino acid substitutions that decrease binding of the Fc domain to an Fc receptor.

According to some embodiments, the humanized antibody has a mutated Fc domain that prevents FcγR-mediated internalization.

According to some embodiments, the humanized antibody comprises a Fc null domain. According to certain embodiments, the Fc domain is null for binding to a Fcγ receptors.

As used herein, an "Fc null" refers to a domain that exhibits weak to no binding to one or more of the Fcγ receptors.

Antibody-Drug Conjugates

According to an aspect, the present invention provides a conjugate comprising the humanized antibody as described herein fused to a toxin.

According to some embodiments, the conjugate comprises an antibody or fragment thereof comprising a heavy chain and a light chain, wherein the heavy chain comprises a variable region having an amino acid sequence at least about 90% identical to a sequence selected from the group consisting of SEQ ID NO: 11, SEQ ID NO: 13, SEQ ID NO: 14, SEQ ID NO: 15 and SEQ ID NO: 16; and wherein the light chain comprises a variable region having an amino acid sequence at least about 90% identical to a sequence selected from the group consisting of SEQ ID NO: 12, SEQ ID NO: 17, SEQ ID NO: 18, SEQ ID NO: 19 and SEQ ID NO: 20.

According to some embodiments, the toxin is selected from the group consisting of microtubule inhibitor, DNA synthesis inhibitor, topoisomerase inhibitor, and RNA polymerase inhibitor. Each possibility represents a separate embodiment of the invention.

According to certain embodiments, the toxin is a microtubule-destroying drug. According to certain exemplary embodiments, the toxin is auristatin or a derivative thereof. According to certain embodiments, the auristatin derivative is monomethyl auristatin E (MMAE) or monomethyl auristatin F (MMAF).

According to some embodiments, the toxin is saponin.

According to some embodiments, the toxin is a maytansine derivative. According to certain embodiments, the maytansine derivative is DM4 or DM1.

According to some embodiments, the toxin is quinoline alkaloid. According to certain embodiments, the quinoline alkaloid is SN-38.

According to additional embodiments, the toxin is selected from the group consisting of MMAE, MMAF, Saporin, DM4, DM1, SN-38, Calicheamicin, DXd, PBD, Duocarmycin, Sandramycin, alpha-Amanitin, Chaetocin, Daunorubicin, 17-AAG, Agrochelin A, Doxorubicin, Methotrexate, Colchicine, Cordycepin, Hygrolidin, Herboxidiene, Ferulenol, Curvulin, Englerin A, Taltobulin, Triptolide, Cryptophycin, and Nemorubicin. Each possibility represents a separate embodiment of the invention.

According to some embodiments, the toxin is a DNA topoisomerase I (TOP1) inhibitor. According to certain embodiments, the DNA topoisomerase I (TOP1) inhibitor is DXd.

The toxins names are used herein as known in the art. Non limiting examples of suitable payloads include:

DM1—a N²'-deacetyl-N²'-(3-mercapto-1-oxopropyl)-maytansine—a tubulin inhibitor.

DM4—a N²'-deacetyl-N²'-(4-mercapto-4-methyl-1-oxo-pentyl)-Ravtansine—a tubulin inhibitor.

SN-38—a potent DNA topoisomerase I inhibitor, a member of the class of pyranoindolizinoquinolines that is (4S)-pyrano[3',4': 6,7]indolizino[1,2-b]quinoline-3,14-dione bearing two additional ethyl substituents at positions 4 and 11 as well as two additional hydroxy substituents at positions 4 and 9.

DXd—an exatecan derivative, a potent DNA topoisomerase I inhibitor (For example Cat. No.: HY-13631D of MCE®).

MMAF—a monomethyl auristatin F—a tubulin inhibitor, having the formula $C_{39}H_{65}N_5O_8$.

MMEA—a monomethyl auristatin E—a tubulin inhibitor, having the formula $C_{39}H_{67}N_5O_7$.

According to some embodiments, the antibody is directly linked to the toxin. According to other embodiments, the antibody and the toxin are linked through a linker. According to some embodiments, the humanized described herein is covalently linked to the toxin.

According to some embodiments, the linker is cleavable. According to additional embodiments, the linker is not cleavable.

According to some embodiments, the linker is cleaved in response to changes in pH or redox potential. According to some embodiments, the linker is cleaved when contacted with lysosomal enzymes.

The present invention provides, according to another aspect, a pharmaceutical composition comprising the humanized antibody or antigen binding fragment described herein or a conjugate comprising the antibody and a pharmaceutically acceptable excipient, carrier, or diluent.

According to other embodiments, the pharmaceutical composition according to the invention is for use in treating cancer characterized by overexpression of Nectin-2. Nectin-2 overexpression related cancer types can be identified using known data bases such as The Cancer Genome Atlas (TCGA). According to certain embodiments, the cancer treatable with a composition according to the present invention is selected from the group consisting of adrenocortical carcinoma (ACC), chromophobe renal cell carcinoma (KICH), liver hepatocellular carcinoma (LIHC), colon and rectal adenocarcinoma (COAD, READ), pancreatic ductal adenocarcinoma (PAAD), pheochromocytoma & paraganglioma (PCPG), papillary kidney carcinoma (KIRP), lung adenocarcinoma (LUAD), head and neck squamous cell carcinoma (HNSC), prostate adenocarcinoma (PRAD), uterine corpus endometrial carcinoma (UCEC), cervical cancer (CESC), cutaneous melanoma (SKCM), mesothelioma (MESO), urothelial bladder cancer (BLCA), clear cell kidney carcinoma (KIRC), lung squamous cell carcinoma (LUSC), uterine carcinosarcoma (UCS), sarcoma (SARC), ovarian serous cystadenocarcinoma (OV), papillary thyroid carcinoma (THCA), glioblastoma multiforme (GBM), breast cancer (BRCA), lower grade glioma (LGG), and diffuse large B-cell lymphoma (DLBC). Each possibility represents a separate embodiment of the invention.

As used herein the term "individual," "patient," or "subject" refers to individuals diagnosed with, suspected of being afflicted with, or at-risk of developing at least one disease for which the described compositions and method are useful for treating. According to some embodiments the individual is a mammal. According to some embodiments, the mammal is a mouse, rat, rabbit, dog, cat, horse, cow, sheep, pig, goat, llama, alpaca, or yak. According to some embodiments, the individual is a human.

As used herein the term an "effective amount" refers to the amount of a therapeutic that causes a biological effect when administered to a mammal. Biological effects include, but are not limited to, inhibition or blockade of a receptor ligand interaction (e.g., PVR-TIGIT, PD-1-PD-L1/PD-L-2), inhibition of a signaling pathway, reduced tumor growth, reduced tumor metastasis, or prolonged survival of an animal bearing a tumor. A "therapeutic amount" is the concertation of a drug calculated to exert a therapeutic effect. A therapeutic amount encompasses the range of dosages capable of inducing a therapeutic response in a population of individuals. The mammal can be a human individual. The human individual can be afflicted with or suspected or being afflicted with a tumor.

As used herein the term "combination" or "combination treatment" can refer either to concurrent administration of the articles to be combined or sequential administration of the articles to be combined. As described herein, when the combination refers to sequential administration of the articles, the articles can be administered in any temporal order.

As used herein "checkpoint inhibitor" refers a drug that inhibits a biological molecule ("checkpoint molecule") produced by an organism that negatively regulates the anti-tumor/cancer activity of T cells in the organism. Checkpoint molecules include without limitation PD-1, PD-L1, PD-L-2, CTLA4, TIM-3, LAG-3, VISTA, SIGLEC7, PVR, TIGIT, IDO, KIR, A2AR, B7-H3, B7H4, CEACAM1, and CD112R.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

The term "treatment" as used herein refers to both therapeutic treatment and prophylactic or preventative measures. Those in need of treatment include those already with the disorder as well as those in which the disorder is to be prevented.

The terms "cancer" and "tumor" relate to the physiological condition in mammals characterized by deregulated cell growth. Cancer is a class of diseases in which a group of cells display uncontrolled growth or unwanted growth. Cancer cells can also spread to other locations, which can lead to the formation of metastases. Spreading of cancer cells in the body can, for example, occur via lymph or blood. Uncontrolled growth, intrusion, and metastasis formation are also termed malignant properties of cancers. These malignant properties differentiate cancers from benign tumors, which typically do not invade or metastasize.

According to some embodiments, the method of treating cancer comprises administering the pharmaceutical composition as part of a treatment regimen comprising administration of at least one additional anti-cancer agent.

According to some embodiments, the anti-cancer agent is selected from the group consisting of an antimetabolite, a mitotic inhibitor, a taxane, a topoisomerase inhibitor, a topoisomerase II inhibitor, an asparaginase, an alkylating agent, an antitumor antibiotic, and combinations thereof. Each possibility represents a separate embodiment of the invention.

According to some embodiments, the antimetabolite is selected from the group consisting of cytarabine, fludarabine, fluorouracil, mercaptopurine, methotrexate, thioguanine, gemcitabine, and hydroxyurea. According to some embodiments, the mitotic inhibitor is selected from the group consisting of vincristine, vinblastine, and vinorelbine. According to some embodiments, the topoisomerase inhibitor is selected from the group consisting of topotecan and irinotecan. According to some embodiments, the alkylating agent is selected from the group consisting of busulfan, carmustine, lomustine, chlorambucil, cyclophosphamide, cisplatin, carboplatin, ifosfamide, mechlorethamine, melphalan, thiotepa, dacarbazine, and procarbazine. According to some embodiments, the antitumor antibiotic is selected from the group consisting of bleomycin, dactinomycin, daunorubicin, doxorubicin, idarubicin, mitomycin, mitoxantrone, and plicamycin. According to some embodiments, the topoisomerase II is selected from the group consisting of etoposide and teniposide. Each possibility represents a separate embodiment of the present invention.

The present invention provides, according to another aspect, a method of treating a cancer in an individual afflicted with a cancer comprising administering to the individual a therapeutically effective amount of the humanized antibody or antigen binding fragment thereof or the pharmaceutical composition, and an inhibitor of PD-1, PD-L1, CTLA-4 or CD112R signaling. In certain embodiments, the cancer comprises a solid tumor. In certain embodiments, the cancer is selected from the group consisting of lung cancer, colon cancer, glioblastoma, pancreatic cancer, breast cancer, bladder cancer, kidney cancer, head and neck cancer, ovarian cancer, cervical cancer, or prostate cancer. In certain embodiments, the inhibitor of PD-1 signaling is an antibody or fragment thereof that binds to PD-1. In certain embodiments, the antibody or fragment thereof that binds to PD-1 is Pembrolizumab, Nivolumab, AMP-514, Tislelizumab, Spartalizumab, or a PD-1 binding fragment thereof. In certain embodiments, the inhibitor of PD-1 signaling is an antibody that specifically binds PD-L-1 or PD-L-2. In certain embodiments, the antibody that specifically binds PD-L1 or PD-L2 comprises Durvalumab, Atezolizumab, Avelumab, BMS-936559, or FAZ053, or a PD-L1 or PD-L2 binding fragment thereof. In certain embodiments, the inhibitor of PD-1 signaling comprises an Fc-fusion protein that binds PD-1, PD-L1, or PD-L2. In certain embodiments, the Fc-fusion protein comprises AMP-224 or a PD-1 binding fragment thereof. In certain embodiments, the inhibitor of PD-1 signaling comprises a small molecule inhibitor of PD-1, PD-L1, or PD-L2. In certain embodiments, the small molecule inhibitor of PD-1, PD-L1, or PD-L2 signaling comprises on or more of: N-{2-[({2-methoxy-6-[(2-methyl[1,1'-biphenyl]-3-yl) methoxy]pyridin-3-yl}methyl)amino]ethyl}acetamide (BMS 202); (2-((3-cyanobenzyl)oxy)-4-((3-(2,3-dihydrobenzo[b][1,4]dioxin-6-yl)-2-methylbenzyl)oxy)-5-methylbenzyl)-D-serine hydrochloride; (2R,4R)-1-(5-chloro-2-((3-cyanobenzyl)oxy)-4-((3-(2,3-dihydrobenzo[b][1,4]dioxin-6-yl)-2-methylbenzyl)oxy)benzyl)-4-hydroxypyrrolidine-2-carboxylic acid; 3-(4,6-dichloro-1,3,5-triazin-2-yl)-1-phenylindole; 3-(4,6-dichloro-1,3,5-triazin-2-yl)-1-phenyl-1h-indole; L-α-Glutamine, N²,N⁶-bis(L-scryl-L-asparaginyl-L-threonyl-L-seryl-L-α-glutamyl-L-seryl-L-phenylalanyl)-L-lysyl-L-phenylalanyl-L-arginyl-L-valyl-L-threonyl-L-glutaminyl-L-leucyl-L-alanyl-L-prolyl-L-lysyl-L-alanyl-L- glutaminyl-L-isoleucyl-L-lysyl; (2S)-1-[[2,6-dimethoxy-4-[(2-methyl[1,1'-biphenyl]-3-yl) methoxy]phenyl]methyl]-2-piperidinecarboxylic acid; Glycinamide, N-(2-mercaptoacetyl)-L-phenylalanyl-N-methyl-L-alanyl-L-asparaginyl-L-prolyl-L-histidyl-L-leucyl-N-methylglycyl-L-tryptophyl-L-seryl-L-tryptophyl-N-methyl-L-norleucyl-N-methyl-L-norleucyl-L-arginyl-L-cysteinyl-, cyclic (1→14)-thioether; or a derivative or analog thereof.

Also described herein is a method of making composition for treating a cancer in an individual afflicted with cancer comprising admixing the humanized antibody or antigen binding fragment thereof and a pharmaceutically acceptable excipient, carrier, or diluent. In certain embodiments, the cancer comprises a solid tumor. In certain embodiments, the cancer is selected from the group consisting of colon cancer, pancreatic cancer, breast cancer, bladder cancer, kidney cancer, head and neck cancer, ovarian cancer, glioblastoma, cervical cancer, prostate cancer, and lung cancer.

Also described herein is a method of producing the humanized antibody or antigen binding fragment thereof comprising incubating the cell line described herein in a cell culture medium under conditions sufficient to allow expression and secretion of the humanized antibody or antigen binding fragment thereof.

According to some particular embodiments, the additional anti-cancer agent is selected from the group consisting of bevacizumab, carboplatin, cyclophosphamide, doxorubicin hydrochloride, gemcitabine hydrochloride, topotecan hydrochloride, thiotepa, and combinations thereof. Each possibility represents a separate embodiment of the present invention.

EXAMPLES

Reference is now made to the following examples, which together with the above descriptions, illustrate the invention in a non-limiting fashion.

Generally, the nomenclature used herein, and the laboratory procedures utilized in the present invention include molecular, biochemical, microbiological, immunological, and recombinant DNA techniques. Such techniques are well known in the art. Other general references referring to well-known procedures are provided throughout this document for the convenience of the reader.

Figure 1B:
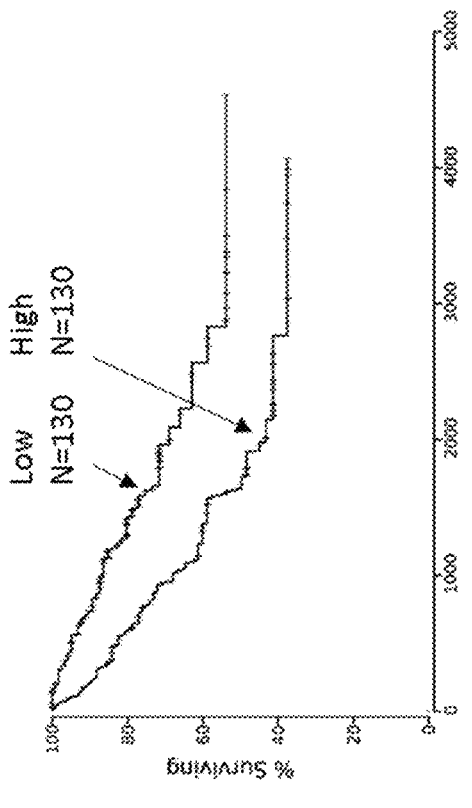
FIGS. 1A-1C depict the correlation of Nectin-2 mRNA levels (high or low as indicated) with survival probability of Low-grade glioma (FIG. 1A), Kidney Renal Clear Cell Carcinoma (FIG. 1B) and lung adenocarcinoma (FIG. 1C) patients. Data sets were obtained from the TCGA site and analyzed using oncolnc.org site (https://doi.org/10.7717/peerj-cs.67). N depicts number of patients included at the analysis.
Figure 1A:
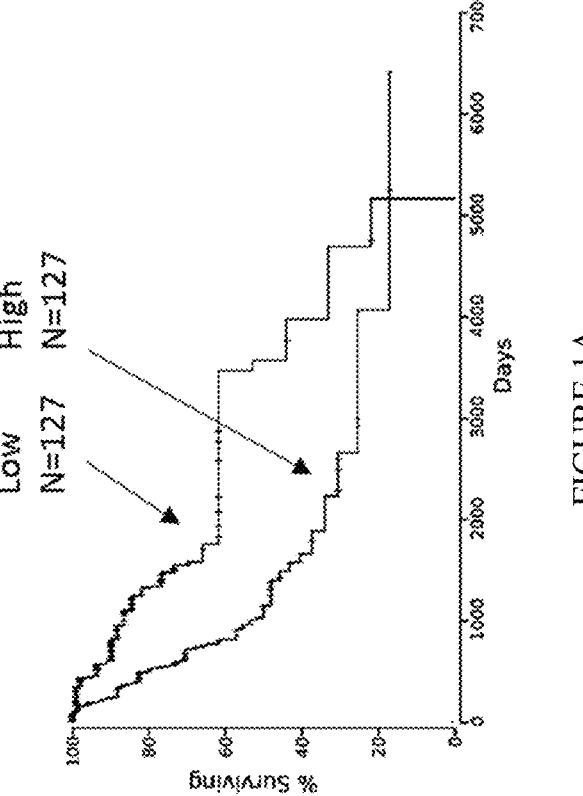
Figure 1C:
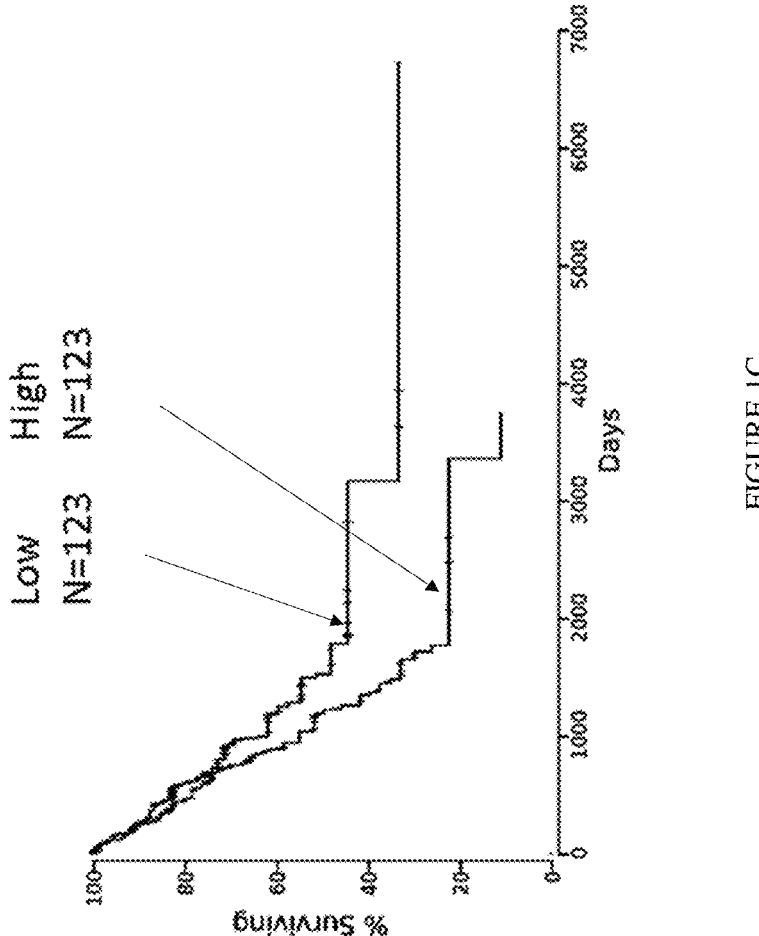

Example 1. High Expression of Nectin-2 mRNA Correlates with Poor Survival Probability of Various Cancer Patients The correlation between Nectin-2 mRNA expression levels and survival probability was examined on data from TCGA site, and analyzed using the oncolnc.org site, (https://doi.org/10.7717/peerj-cs.67). Nectin-2 mRNA expression levels were the basis for dividing patients for two subgroups of low and high expressors, as indicated by the arrows in FIG. 1 for Low grade glioma (FIG. 1A; p=5.22E-5), Kidney Renal Clear Cell Carcinoma (FIG. 1B; p=0.00037) and lung adenocarcinoma (FIG. 1C; p=0.0319) patients.

Example 2. Nectin-2 Binds and Affects Immune Cells Through Specific Receptors

Figure 2:
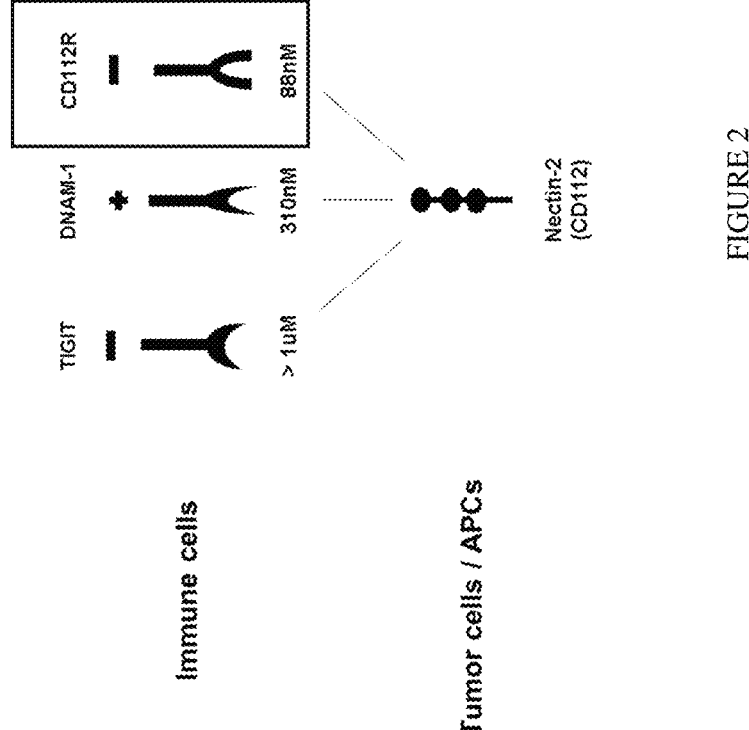
FIG. 2 is a schematic illustration of receptors expressed on immune cells and their respective affinities to Nectin-2 (CD112), which is expressed by tumors or on antigen presenting cells (APCs). TIGIT is a co-inhibitory receptor on many immune cells (e.g., T and NK cells); DNAM-1

The schematic illustration of FIG. 2 demonstrates receptors expressed on immune cells and their respective affinities to Nectin-2 expressed by tumors or on antigen presenting cells (APCs). TIGIT relates to a co-inhibitory receptor on immune cells such as T and NK cells; DNAM-1 (also termed CD226) relates to an activating receptor on immune cells (e.g., T cells), and CD112R (also termed PVRIG) relates to a co-inhibitory receptor on lymphoid immune cells (e.g., T and NK cells); Nectin-2 (CD112) servs as an inhibitory ligand for immune cells, mainly via its binding to CD112R. According to the present invention, humanized anti-Nectin-2 mAbs block Nectin-2 interactions with its high affinity receptor CD112R and may target cancer cells for specific toxin delivery and killing.

Example 3. Nectin-2 is Expressed on the Majority of Solid Tumors

The database Proteinatlas.com was searched for all the aliases of Nectin-2 (NECTIN2, CD112, HVEB, PRR2, PVRL2, PVRR2). Under the pathology rubric, data using three different mAbs was found. HPA0127569 mAb has the highest validation score (Enhanced) as it was validated by orthogonal method. Thus, the expression data across different tumors was selected for this clone only, and is depicted in FIG. 3. The graph is showing percent of tumors positive for Nectin-2 expression. In 17/20 indications membranous expression of Nectin-2 is seen at Moderate-High levels.

Example 4. Improved Properties of Humanized Anti-Nectin-2 mAbs

Murine anti-human Nectin-2 clone 2.11, disclosed in Patent application publication No. WO2020144697, was selected as the lead mAb for humanization. Based on structural analysis, a large preliminary set of sequence segments were identified that were used to create the humanized variants. These segments were selected and analyzed using iTope™ technology for in silico analysis of peptide binding to human MHC class II alleles (Perry et al., 2008) and using the TCED™ of known antibody sequence-related T cell epitopes (Bryson et al., 2010). Sequence segments that were identified as significant non-human germline binders to human MHC class II, or that scored significant hits against the TCED™, were discarded. This resulted in a reduced set of segments, and combinations of these were further analyzed, as described above, to ensure that the junctions between segments did not contain potential T cell epitopes. Selected sequence segments were assembled into complete V region sequences that were devoid of significant T cell epitopes. Five heavy chain (VH1 to VH5) and 5 light chain (VK1 to VK5) sequences were then chosen. The data at Table 1 present the readout of the iTope™ algorithm. To reduce the potential for anti-drug antibody (ADA) generation, the sequence of the mAbs was analyzed for potential binding of MHCI1. The main risk is linked to the high affinity binding peptides, which are separated from the moderated affinity binding peptides.

TABLE 1

Improved characteristics of the humanized anti-Nectin-2 mAbs. Illustration of predicted MHCII epitopes (iTope score) of the parental (V0) and humanized heavy (VH1-5) and light (Vk1-5) variable chains used to generate humanized variants for lead drug selection.

| Predicted affinity MHCII | Heavy Chain | | | | | |
|---|---|---|---|---|---|---|
| | VH0 | VH1 | VH2 | VH3 | VH4 | VH5 |
| Moderate | 5 | 6 | 4 | 4 | 4 | 3 |
| High | 8 | 4 | 3 | 3 | 1 | 1 |

22

TABLE 1-continued

Improved characteristics of the humanized anti-Nectin-2 mAbs. Illustration of predicted MHCII epitopes (iTope score) of the parental (V0) and humanized heavy (VH1-5) and light (Vk1-5) variable chains used to generate humanized variants for lead drug selection.

| Predicted affinity MHCII | Light Chain | | | | | |
|---|---|---|---|---|---|---|
| | Vk0 | Vk1 | Vk2 | Vk3 | Vk4 | Vk5 |
| Moderate | 8 | 4 | 3 | 3 | 3 | 1 |
| High | 4 | 3 | 3 | 2 | 2 | 2 |

The parental heavy chain (VH0) has 8 predicted high affinity motifs and the parental light chain (Vk0) has 4 such motifs. Following the humanization process, the number of predicted high affinity MHCII epitopes for the heavy chain was reduced to 3 (VH2, VH3) or even to 1 (VH4, VH5) and for the light chain the predicted high affinity MHCII motifs were reduced to 2 (VK3-5).

Thus, the humanization process eliminated the majority of the predicted high affinity MHCII motifs that may trigger immunogenicity against the mAb.

Stability of the humanized variants was assessed by thermal ramp stability experiments that are well established methods for ranking proteins and formulations for stability. A protein's denaturation profile provides information about its thermal stability and represents a structural 'fingerprint' for assessing structural and formulation buffer modifications. A widely used measure of the thermal structural stability of a protein is the temperature at which it unfolds from the native state to a denatured state.

For many proteins, this unfolding process occurs over a narrow temperature range and the mid-point of this transition is termed 'melting temperature' or 'Tm'. To determine the melting temperature of a protein, UNcle measures the fluorescence of Sypro Orange (which binds to exposed hydrophobic regions of proteins) as the protein undergoes conformational changes. Increased Tm is a desired characteristic in Ab lead selection as it predicts a more stable Ab.

Purified lead humanized antibody variants, in duplicates, were diluted to a final test concentration of 0.5 mg/ml in PBS into which Sypro Orange (at 160× Stock solution) was added to a final concentration of 20× solution. 9 µL of each sample mixture was loaded in duplicate into UNi microcuvettes. Samples were subjected to a thermal ramp from 15-95° C., with a ramp rate of 0.3° C./minute and excitation at 473 nm. Full emission spectra were collected from 250-720 nm, and the area under the curve between 510-680 nm was used to calculate the inflection points of the transition curves (Tonset and Tm). As seen in Table 2, for all of the antibodies tested, Tm1 and Tonset are higher for the humanized variants compared with the chimeric antibody (VH0/VK0).

TABLE 2

A summary of thermal stability values for the parental/chimeric (VH0/Vk0) antibody and for six purified lead humanized variants as determined using the UNcle biostability platform.

| Variant | Average Tonset (° C.) | Average Tm1 (° C.) |
|---|---|---|
| VH0/Vκ0 | 58.1 | 67.3 |
| VH3/Vκ3 | 65.6 | 74.3 |
| VH4/Vκ2 | 60.7 | 71.9 |

TABLE 2-continued

A summary of thermal stability values for the parental/chimeric
(VH0/Vk0) antibody and for six purified lead humanized
variants as determined using the UNcle biostability platform.

| Variant | Average Tonset (° C.) | Average Tm1 (° C.) |
|---|---|---|
| VH4/Vκ3 | 60.6 | 70.8 |
| VH5/Vκ3 | 58.8 | 72.7 |
| VH5/Vκ4 | 59.9 | 68.3 |
| VH5/Vκ5 | 61.3 | 69.4 |

Improved stability of both Tonset and TM1 (measuring of unfolding) above 5 degrees
Celsius, was considered significant and is marked in bold fonts.

Example 5. Improved Binding to Nectin-2, and Blocking of CD112R Binding by the Humanized Anti-Nectin-2 mAbs The humanized anti-Nectin-2 mAbs binding to human Nectin-2 expressed by 293T cells, (protein id: Q92692) and Chlorocebus (African green monkey, AFG) Vero cells were assessed and EC50 values were established. AFG expresses Nectin-2 protein (XP_007995342.1) with 97% similarity to human Nectin-2. FIGS. 4A and 4B depict fold change of EC50 values to human and AFG cells expressed Nectin-2, respectively. Both cell lines were plated at $0.5 \times 10^5$ cells per well. The chimeric (HOKO) and humanized mAbs were added at concentration range of 20-0.001 nM. For detection, anti-human-APC Ab was used at 1:200 dilution (Jackson Immunoresearch AB_2340526). Cells were analyzed by FACS and EC50 was calculated and compared to that of the chimeric Ab (fold improve). This analysis revealed improved binding of the humanized variants, and similar degree of cross-reactivity to monkey Nectin-2, comparing to the chimeric mAb (FIGS. 4A vs. 4B). To evaluate the blocking capacity of the humanized Abs, human Nectin-2 was overexpressed in Chinese hamster ovary (CHO) cells. FIG. 4C shows data generated when $10^5$ of CHO-hNectin-2/well were incubated with 30 nM of human CD112R-mIgG2a in presence of the indicated humanized Abs, in concentrations ranging from 66-0.81 nM. Bound CD112R was detected by using amIgG2a-647 (Jackson Immunoresearch Cat 115-607-186) at 1:200 dilution followed by FACS analysis. As can be seen, all humanized variants maintained full blocking capacity.

Example 6. Anti-hNectin-2 Humanized Variant H3K3 can Serve as an ADC Driver in an Fc Independent Manner To assess the capacity of the mAbs to serve as ADCs, the streptavidin-saporin (ZAP), IT-27-250 (ATS), was used. The mAbs indicated in FIG. 5 were biotinylated using the biotinylation kit Ab207195 (Abcam) at 1:1 ratio. FIG. 5A depicts the results of the initial screen which included top humanized clones and A549 (lung adenocarcinoma) cells as targets. $2 \times 10^3$ cells per well were plated and allowed to adhere over 4-6 hours period. The ADCs were added, and the cells were incubated with the ADCs. After 72 hours, the assay was harvested and tumor cell killing was evaluated using CellTiter-Glo® 2.0 Cell Viability Assay-(Promega G9242) following standard protocol. Only clone H3K3 showed robust killing. Next, clone H3K3 was directly compared to clone H4K2 (FIG. 5B). Both clones exhibited robust killing, and H3K3 was selected for future analysis due to superior developability properties. The chimeric parental clone and the FcgR$^{null}$ variant (IgG2-P238H) (In FcgR$^{null}$, the g is for gamma or γ) of clone H3K3 (IgG1) were tested under the above conditions and results are shown in FIG. 5C. Significant killing (p<0.001) by both the chimeric and humanized H3K3 variants was seen at all concentrations of these ADCs, and the FcgR$^{null}$ variant led to identical level of target cell killing compared to the hIgG1 clone.

Example 7. Anti-hNectin-2 H3K3-FcgR$^{null}$ ADCs Lead to Robust Killing of Solid Tumor Cell Lines In-Vitro Additional H3K3-FcgR$^{null}$ mAbs were generated by mutating key residues in the hinge region of human IgG1 as indicated in Table 3.

TABLE 3

A summary of the Fc-substitution for the humanized IgG1
FcgR$^{null}$ linker-payload combinations, release mechanisms, and
the relevant drug-to-antibody ratios (DARs) for the H3K3-based ADCs.

| Fc-Mutation (FcgR$^{null}$) | Linker | Payload | Release mechanism | Average DAR (LC-MS) |
|---|---|---|---|---|
| hIgG1 G237I | MC-VC-PAB | MMAE | Proteolytic cleavage | 4.3 |
| hIgG1 G237I | MC | MMAF | Degradation | 4.2 |
| hIgG1 L235S | SMCC | DM1 | Degradation | 4.0 |
| hIgG1 L235S | SPDB | DM4 | Redox | 4.2 |
| hIgG1 L235S/G237I | Lys-PAB-CO | SN38 | pH | 8 |

The presented linker payload combinations were chosen according to the desired release mechanism and were generated according to the standard protocol by Abzena LTD. Briefly, the mAbs were reduced and incubated with an excess of the linker-payload to obtain the desired drug antibody ratio (DAR) of 4 for all the linker-payloads except for SN-38, which had a target DAR of 8. The final products were then purified, and the DARs were established by LC/MS method. Selected tumor cell lines, representing various solid tumors, were used to assess potency of the various linker-payload combinations in-vitro. The indicated target cells were plated at $2 \times 10^3$ cells per well and allowed to adhere over 4-6 hours period. The ADCs were added at concentrations of 4-0.16 ug/ml using 5-fold dilutions, and the cells were incubated with the ADCs. After 72 hours, the assay was harvested and tumor cell killing was evaluated using CellTiter-Glo® 2.0 Cell Viability Assay—(Promega G9242) following standard protocol. Robust killing of RKO cells (colorectal adenocarcinoma), MDA-MB-231 cells (triple negative breast cancer) and of A549 cells (lung adenocarcinoma) is depicted in FIGS. 6A-6C, respectively. Killing of target cells was significant (p<0.001) by two-tailed student t-test, unless indicated by NS (not significant, p>0.05).

Example 8. Selected FcgR$^{null}$ Mutations Prevent ADC Killing Via FcgR

To evaluate the degree of non-target specific killing by the humanized anti-Nectin-2 ADCs, which is due to the Ab Fc binding to its FcγR, and which may contribute to non-specific effect of the ADC, CHO cells overexpressing the high affinity Fc receptor hCD64 (CHO-hCD64) were generated. These cells do not express human Nectin-2 and thus no target-specific killing is expected. Parental CHO cells and CHO-hCD64 were plated at $2 \times 10^3$ cells per well and allowed to adhere over 4-6 hours. The different Fc variant ADCs were added at 12 ug/ml. After incubation of 72 hours, the assay was harvested and tumor cell killing was evaluated using CellTiter-Glo® 2.0 Cell Viability Assay-(Promega G9242).

As seen in FIG. 7, both the IgG4-S228P and the hIgG1-positive controls, led, as expected, to significantly higher degree of the killing of the CHO-hCD64 cells compared to parental CHO cells. On the other hand, the IgG1 G237I substitution resulted in similar low-level of killing of both parental and hCD64 overexpressing cells (non-specific killing). These results confirm that the FogRnull variant is not bound and internalized by the high affinity FcgR CD64.

Example 9. Anti-hNectin-2 Humanized H3K3-FcgR$^{null}$ ADCs Lead to Robust Killing of the Hematological Tumor Cell Line HL-60 In-Vitro HL-60 cells (AML model) were plated at $2\times10^3$ cells per well and the ADCs were added at concentrations of 9-1 μg/ml, using 3-fold dilutions. The cells were incubated with the ADCs for 72 hours. Then, the assay was harvested and tumor cell killing was evaluated using CellTiter-Glo® 2.0 Cell Viability Assay—(Promega G9242) as described above. As seen in FIG. 8, except for the DM1 payload (indicated in the graph), all other compounds led to significant killing of the targets in all concentrations tested and all exceeded 90% killing at the highest concentration (>60 nM). Based on these results the SMCC-DM1 linker payload was excluded from future experiments.

Example 10. Anti-hNectin-2 H3K3-FcgR$^{null}$-MC-VC-PAB-MMAE ADC Leads to Tumor Regression in an Aggressive AML Model Nude female mice (n=25) were injected s.c. with $10\times10^6$ HL-60 cells in 1:1 Matrigel. Once tumors reached an average volume of 205 mm$^3$, mice were randomized into five groups (n=5 per group) and treated in a blinded manner, by i.v. injection of either PBS (vehicle), H3K3-FcgR$^{null}$_M-MAE, H3K3-FcgR$^{null}$-MMAF, H3K3-FcgR$^{null}$-DM4 or H3K3-FcgR$^{null}$-SN-38. All treatments were at 5 mg/kg, given every 4 days, for 4 consecutive doses. As can be seen in FIG. 9A, on day 23 after randomization, H3K3-FcgR$^{null}$-MMAF and the SN-38 variants did not attenuate tumor growth. H3K3-FcgR$^{null}$-DM4 led to significant tumor growth inhibition (TGI) of 49%, while H3K3-FcgR$^{null}$-MMAE led to significant tumor regression. FIG. 9B shows the mean effect of H3K3-FcgR$^{null}$-MMAE.

Example 11. Anti-hNectin-2 H3K3-FcgR$^{null}$-MC-VC-PAB-MMAE ADC Leads to Tumor Regression in an Aggressive Colon Adenocarcinoma Model Nude female mice (n=5 per group) were injected SC with $5\times10^6$ RKO cells in 1:1 Matrigel. Once tumors reached an average volume of 160 mm$^3$, mice were randomized into two groups and treated every 4 days, in a blinded manner, by i.v. injection of either PBS (Vehicle) or H3K3-FcgR$^{null}$-MMAE (1107-MC-VC-MMAE) at 5 mg/kg for 4 consecutive doses. On day 13 after randomization, H3K3-FcgR$^{null}$-MMAE, led to significant tumor regression, as can be seen in FIG. 10, representing >80% TGI compared to vehicle treated group.

Example 12. Anti-hNectin-2 H3K3-FcgR$^{null}$ mAb has Similar In Vitro Killing Activity Compared to Trodelvy For the in vitro killing assay (FIG. 11) MDA-MB-231 target cells were plated at $2\times10^3$ cells per well and allowed to adhere over 4-6 hours. Next, H3K3-FcgR$^{null}$ anti-Nectin-2 mAb (NTX1107) linked to Dxd, and Trodelvy (Sacituzumab govitecan), an approved ADC drug for TNBC, were added at concentrations of 12 ug/ml (dark grey bars) and 3 ug/ml (light grey bars). Of note, both ADCs use the same class of cytotoxic payload (i.e., topoisomerase I (TOP1) inhibitors). The cells were incubated with the ADCs for 120 hours, after which tumor cell killing was evaluated using CellTiter-Glo® 2.0 Cell Viability Assay-(Promega G9242), following a standard protocol. Robust killing of MDA-MB-231 cells was induced by both ADCs with significant superiority of Trodelvy at both concentrations (*** p<0.0005).

Example 13. Anti-hNectin-2 H3K3-FcgR$^{null}$ Conjugated to Topoisomerase 1 Inhibitor, but not Trodelvy, Inhibits In Vivo Growth of Aggressive MDA-MB-231 Tumors Nude female mice (n=7 per group) were injected s.c. with $5\times10^6$ MDA-MB-231 cells in 1:1 Matrigel. Once tumors reached an average volume of 230 mm$^3$ mice were randomized into treatment groups and treated every 4 days, for 3 consecutive doses, in a blinded manner, by i.v. injection of either PBS (vehicle), NTX1107-Dxd, or Trodelvy at 5 mg/kg. There was no effect for Trodelvy treatment on the tumor growth.

As seen in FIG. 12, NTX1107-Dxd was able to significantly inhibit tumor growth (*p<0.02, <0.005.* p<0.0005). These findings were unexpected since the in-vitro killing potency of Trodelvy was higher than that of NTX1107-Dxd FIG. 11), and Trodelvy is an approved ADC for TNBC. These observations suggest that anti-Nectin-2 (NTX1107) is a uniquely potent ADC for the treatment of solid tumors.

Example 14. Anti-hNectin-2 H3K3-FcgR$^{null}$ can Regress Aggressive MDA-MB-231 Tumors In Vivo when Conjugated to Tubulin or TOP1 Targeting Agents Nude female mice (n=7 per group) were injected s.c. with $5\times10^6$ MDA-MB-231 cells in 1:1 Matrigel. Once tumors reached an average volume of 210 mm$^3$ mice were randomized into treatment groups and treated every 4 days, for 5 consecutive doses, in a blinded manner, by i.v. injection of either PBS (vehicle), H3K3-FcgR$^{null}$ (NTX1107)-MMAE, or NTX1107-Dxd. As can be seen in FIG. 13, all animals treated with NTX1107-MMAE had no detectable tumors at the end of the study. For the animals treated with NTX1107-Dxd, four had no tumors, while for the remaining three the average tumor volume was 210 mm$^3$, indicating tumor stasis. These findings suggest that the humanized antibodies targeting Nectin-2 described herein (NTX1107) may form uniquely potent ADCs for treatment of solid tumors, when using payloads of various classes.

Sequences

TABLE 4

CDR sequences:

| Description | KABAT | IMGT | Overlapping sequence |
|---|---|---|---|
| Heavy Chain CDR1 | SYWIH (SEQ ID NO: 1) | GYIFTSYW (SEQ ID NO: 7) | SYW |
| Heavy Chain CDR2 | AVYPGNSDSNYNQKF(KA/QG) (SEQ ID NO: 2) | VYPGNSDS (SEQ ID NO: 8) | SEQ ID NO: 8 |
| Heavy Chain CDR3 | LVGTFDY (SEQ ID NO: 3) | TKLVGTFDY (SEQ ID NO: 9) | SEQ ID NO: 3 |
| Light Chain CDR1 | (K/R)ASQNVGINV(V/A) (SEQ ID NO: 4) | QNVGIN (SEQ ID NO: 10) | SEQ ID NO: 10 |
| Light Chain CDR2 | SASYRYS (SEQ ID NO: 5) | SAS | SAS |
| Light Chain CDR3 | QQYNTNPFT (SEQ ID NO: 6) | SEQ ID NO: 6 | SEQ ID NO: 6 |

- heavy chain variable region NT20-11_VH3
SEQ ID NO: 11
QVQLVQSGAEVKKPGSSVKVSCKASGYIFTSYWIHWVRQPPGKGLEWIG

AVYPGNSDSNYNQKFKARVTITAVTSTSTAYMELSSLRSEDTAVYYCTK

LVGTFDYWGQGTTVTVSS light chain variable region NT20-11_Vk3
SEQ ID NO: 12
DIQMTQSPSTLSASVGDRVSVTCKASQNVGINVVWYQQKPGQPPKTLIY

SASYRYSGVPDRFSGSGSGTDFTLTISSLQAEDLAEYFCQQYNTNPFTF

GQGTKLEIK

- heavy chain variable region NT20-11_VH1
SEQ ID NO: 13
EVQLVQSGTELKKPGSSVKVSCKASGYIFTSYWIHWVRQPPGKGLEWIG

AVYPGNSDSNYNQKFKARATITAVTSTSTAYMELSSLTSEDSAVYYCTK

LVGTFDYWGQGTTVTVSS

- heavy chain variable region NT20-11_VH2
SEQ ID NO: 14
EVQLVQSGAEVKKPGSSVKVSCKASGYIFTSYWIHWVRQPPGKGLEWIG

AVYPGNSDSNYNQKFKARATITAVTSTSTAYMELSSLRSEDTAVYYCTK

LVGTFDYWGQGTTVTVSS

- heavy chain variable region NT20-11_VH4
SEQ ID NO: 15
QVQLVQSGAEVKKPGSSVKVSCKASGYIFTSYWIHWVRQPPGKGLEWIG

AVYPGNSDSNYNQKFQGRVTITAVTSTSTAYMELSSLRSEDTAVYYCTK

LVGTFDYWGQGTTVTVSS

-continued

- heavy chain variable region NT20-11_VH5
SEQ ID NO: 16
QVQLVQSGAEVKKPGSSVKVSCKASGYIFTSYWIHWVRQPPGKGLEWIG

AVYPGNSDSNYNQKFQGRVTIADESTSTAYMELSSLRSEDTAVYYCTK

LVGTFDYWGQGTTVTVSS

- light chain variable region NT20-11_Vk1
SEQ ID NO: 17
DIVMTQSPSFLSASVGDRVSVTCKASQNVGINVVWYQQRAGQPPKTLIY

SASYRYSGVPDRFTGSGSGTDFTLTISSLQSEDLAEYFCQQYNTNPFTF

GQGTKLEIK

- light chain variable region NT20-11_Vk2
SEQ ID NO: 18
DIVMTQSPSTLSASVGDRVSVTCKASQNVGINVVWYQQKPGQPPKTLIY

SASYRYSGVPDRFTGSGSGTDFTLTISSLQAEDLAEYFCQQYNTNPFTF

GQGTKLEIK

- light chain variable region NT20-11_Vk4
SEQ ID NO: 19
DIQMTQSPSTLSASVGDRVTITCRASQNVGINVVWYQQKPGQPPKTLIY

SASYRYSGVPDRFSGSGSGTDFTLTISSLQAEDVAVYYCQQYNTNPFTF

GQGTKLEIK

- light chain variable region NT20-11_Vk5
SEQ ID NO: 20
DIQMTQSPSTLSASVGDRVTITCRASQNVGINVAWYQQKPGQPPKTLIY

SASYRYSGVPDRESGSGSGTDFTLTISSLQAEDVAVYYCQQYNTNPFTF

GQGTKLEIK

TABLE 5

Framework (Non-CDR) sequences of the humanized heavy chain variable regions.

| Chain | FR-H1 | FR-H2 | FR-H3 | FR-H4 |
|---|---|---|---|---|
| VH3 | QVQLVQSGAEVKKPGSSV KVSCKASGYIFT (SEQ ID NO: 21) | WVRQPPGKGLEWI G (SEQ ID NO: 22) | RVTITAVTSTSTAYM ELSSLRSEDTAVYYC TK (SEQ ID NO: 23) | WGQGTTVTV SS (SEQ ID NO: 24) |

TABLE 5-continued

| Chain | FR-H1 | FR-H2 | FR-H3 | FR-H4 |
|-------|-------|-------|-------|-------|
| | Framework (Non-CDR) sequences of the humanized heavy chain variable regions. | | | |
| VH1 | EVQLVQSGTELKKPGSSV KVSCKASGYIFT (SEQ ID NO: 25) | WVRQPPGKGLEWI G (SEQ ID NO: 22) | RATITAVTSTSTAYM ELSSLTSEDSAVYYCT K (SEQ ID NO: 26) | WGQGTTVTV SS (SEQ ID NO: 24) |
| VH2 | EVQLVQSGAEVKKPGSSV KVSCKASGYIFT (SEQ ID NO: 27) | WVRQPPGKGLEWI G (SEQ ID NO: 22) | RATITAVTSTSTAYM ELSSLRSEDTAVYYC TK (SEQ ID NO: 28) | WGQGTTVTV SS (SEQ ID NO: 24) |
| VH4 | QVQLVQSGAEVKKPGSSV KVSCKASGYIFT (SEQ ID NO: 21) | WVRQPPGKGLEWI G (SEQ ID NO: 22) | RVTITAVTSTSTAYM ELSSLRSEDTAVYYC TK (SEQ ID NO: 23) | WGQGTTVTV SS (SEQ ID NO: 24) |
| VH5 | QVQLVQSGAEVKKPGSSV KVSCKASGYIFT (SEQ ID NO: 21) | WVRQPPGKGLEWI G (SEQ ID NO: 22) | RVTITADESTSTAYM ELSSLRSEDTAVYYC TK (SEQ ID NO: 29) | WGQGTTVTV SS (SEQ ID NO: 24) |

TABLE 6

| Chain | FR-L1 | FR-L2 | FR-L3 | FR-L4 |
|-------|-------|-------|-------|-------|
| | Framework (Non-CDR) sequences of the humanized light variable regions. | | | |
| LK3 | DIQMTQSPSTLSASVGDR VSVTC (SEQ ID NO: 30) | WYQQKPGQPPKTLIY (SEQ ID NO: 31) | GVPDRFSGSGSGTDF TLTISSLQAEDLAEYF C (SEQ ID NO: 32) | FGQGTKLEI K (SEQ ID NO: 33) |
| LK1 | DIVMTQSPSFLSASVGDR VSVTC (SEQ ID NO: 34) | WYQQRAGQPPKTLIY (SEQ ID NO: 35) | GVPDRFTGSGSGTDF TLTISSLQSEDLAEYF C (SEQ ID NO: 36) | FGQGTKLEI K (SEQ ID NO: 33) |
| LK2 | DIVMTQSPSTLSASVGDR VSVTC (SEQ ID NO: 37) | WYQQKPGQPPKTLIY (SEQ ID NO: 31) | GVPDRFTGSGSGTDF TLTISSLQAEDLAEYF C (SEQ ID NO: 38) | FGQGTKLEI K (SEQ ID NO: 33) |
| LK4 | DIQMTQSPSTLSASVGDR VTITC (SEQ ID NO: 39) | WYQQKPGQPPKTLIY (SEQ ID NO: 31) | GVPDRFSGSGSGTDF TLTISSLQAEDVAVYY C (SEQ ID NO: 40) | FGQGTKLEI K (SEQ ID NO: 33) |
| LK5 | DIQMTQSPSTLSASVGDR VTITC (SEQ ID NO: 39) | WYQQKPGQPPKTLIY (SEQ ID NO: 31) | GVPDRFSGSGSGTDF TLTISSLQAEDVAVYY C (SEQ ID NO: 40) | FGQGTKLEI K (SEQ ID NO: 33) |

- HC CDR2                                                        SEQ ID NO: 41

AVYPGNSDSNYNQKFKA

- HC CDR2                                                        SEQ ID NO: 42

AVYPGNSDSNYNQKFQG

- LC CDR1                                                        SEQ ID NO: 43

KASQNVGINVV

- LC CDR1                                                        SEQ ID NO: 44

KASQNVGINVA

- LC CDR1                                                        SEQ ID NO: 45

RASQNVGINVV

- LC CDR1                                                        SEQ ID NO: 46

RASQNVGINVA

-continued

- amino acid sequence of VH3 Full length hIgG1 heavy chain

SEQ ID NO: 47

QVQLVQSGAEVKKPGSSVKVSCKASGYIFTSYWIHWVRQPPGKGLEWIGAVYPGNS

DSNYNQKFKARVTITAVTSTSTAYMELSSLRSEDTAVYYCTKLVGTFDYWGQGTTV

TVSSASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKRVEPKSCDKTHTCPPC

PAPELLGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQ

PREPQVYTLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK

- DNA Sequence VH3 Full length hIgG1

SEQ ID NO: 48 caggtgcagctggtgcagagcggcgcgggaagtgaaaaaaccgggcagcagcgtgaaagtg agctgcaaagcgagcggctatatttttaccagctattggattcattgggtgcgccagccg ccgggcaaaggcctggaatggattggcgcggtgtatccgggcaacagcgatagcaactat aaccagaaatttaaagcgcgcgtgaccattaccgcggtgaccagcaccagcaccgcgtat atggaactgagcagcctgcgcagcgaagataccgcggtgtattattgcaccaaactggtg ggcacctttgattattggggccagggcaccaccgtgaccgtgagcagcgcgagcaccaaa ggcccgagcgtgtttccgctggcgccgagcagcaaaagcaccagcggcggcaccgcggcg ctgggctgcctggtgaaagattattttccggaaccggtgaccgtgagctggaacagcggc gcgctgaccagcggcgtgcatacctttccggcggtgctgcagagcagcggcctgtatagc ctgagcagcgtggtgaccgtgccgagcagcagcctgggcacccagacctatatttgcaac gtgaaccataaaccgagcaacaccaaagtggataaacgcgtggaaccgaaaagctgcgat aaaacccatacctgcccgccgtgcccggcgccggaactgctgggcggcccgagcgtgttt ctgtttccgccgaaaccgaaagatacctgatgattagccgcaccccggaagtgacctgc gtggtggtggatgtgagccatgaagatccggaagtgaaatttaactggtatgtggatggc gtggaagtgcataacgcgaaaaccaaaccgcgcgaagaacagtataacagcacctatcgc gtggtgagcgtgctgaccgtgctgcatcaggattggctgaacggcaaagaatataaatgc aaagtgagcaacaaagcgctgccggcgccgattgaaaaaaccattagcaaagcgaaaggc cagccgcgcgaaccgcaggtgtatacctgccgccgagccgcgaagaaatgaccaaaaac caggtgagcctgacctgcctggtgaaaggcttttatccgagcgatattgcggtggaatgg gaaagcaacggccagccggaaaacaactataaaaccacccgccggtgctggatagcgat ggcagctttttttctgtatagcaaactgaccgtggataaaagccgctggcagcagggcaac gtgtttagctgcagcgtgatgcatgaagcgctgcataaccattatacccagaaaagcctg agcctgagcccgggcaaa

- amino acid sequence of Vk3 Full length Kappa light chain

SEQ ID NO: 49

DIQMTQSPSTLSASVGDRVSVTCKASQNVGINVVWYQQKPGQPPKTLIYSASYRYSG

VPDRESGSGSGTDFTLTISSLQAEDLAEYFCQQYNTNPFTFGQGTKLEIKRTVAAPSV

FIFPPSDEQLKSGTASVVCLLNNFYPREAKVQWKVDNALQSGNSQESVTEQDSKDST

YSLSSTLTLSKADYEKHKVYACEVTHQGLSSPVTKSFNRGEC

-continued

- DNA Sequence Vk3 Full length Kappa
                                                    SEQ ID NO: 50
gatattcagatgacccagagcccgagcaccctgagcgcgagcgtgggcgatcgcgtgagc gtgacctgcaaagcgagccagaacgtgggcattaacgtggtgtggtatcagcagaaaccg ggccagccgccgaaaaccctgatttatagcgcgagctatcgctatagcggcgtgccggat cgctttagcggcagcggcagcggcaccgattttaccctgaccattagcagcctgcaggcg gaagatctggcggaatattttgccagcagtataacaccaacccgtttacctttggccag ggcaccaaactggaaattaaacgcaccgtggcggcgccgagcgtgtttatttttccgccg agcgatgaacagctgaaaagcggcaccgcgagcgtggtgtgcctgctgaacaacttttat ccgcgcgaagcgaaagtgcagtggaaagtggataacgcgctgcagagcggcaacagccag gaaagcgtgaccgaacaggatagcaaagatagcacctatagcctgagcagcaccctgacc ctgagcaaagcggattatgaaaaacataaagtgtatgcgtgcgaagtgacccatcagggc ctgagcagcccggtgaccaaaagctttaaccgcggcgaatgc SEQ ID NO: 51 - VH3 nucleic acids SEQ ID NO: 52 - VH1 nucleic acids SEQ ID NO: 53 - VH2 nucleic acids SEQ ID NO: 54 - VH4 nucleic acids SEQ ID NO: 55 - VH5 nucleic acids SEQ ID NO: 56 - Vk3 nucleic acids SEQ ID NO: 57 - Vk1 nucleic acids SEQ ID NO: 58 - Vk2 nucleic acids SEQ ID NO: 59 - Vk4 nucleic acids SEQ ID NO: 60 - Vk5 nucleic acids SEQ ID NO: 61 - Human IgG1 (L235S) (including VH3)

SEQ ID NO: 62 - Human IgG1 (L235S/E272K) (including VH3)

SEQ ID NO: 63 - Human IgG1 (G237I) (including VH3)

SEQ ID NO: 64 - Human IgG1 (G237I/E272I) (including VH3)

SEQ ID NO: 65 - Human IgG1 (G237I/V264R) (including VH3)

SEQ ID NO: 66 - Human IgG1 (V215A/E269R/K322A) (including VH3)

SEQ ID NO: 67 - Human IgG1 (L234A/L235A/P329G) (including VH3)

SEQ ID NO: 68 - Human IgG4 (S228P/L235P/V264R) (including VH3)

SEQ ID NO: 69 - Human IgG2 (P238H) (including VH3)

SEQ ID NO: 70 - Human IgG2 (P238H/V264R) (including VH3)

SEQ ID NO: 71 - Leader peptide sequence.

The invention claimed is:

1. A conjugate, comprising:

(a) an antibody that binds Nectin-2 or an antigen-binding fragment thereof that comprises:

A) a heavy chain variable region (VH) comprising an amino acid sequence at least 90% identical to the amino acid sequence set forth in SEQ ID NO: 11 and (i) a complementarity determining region (CDR) 1 having an amino acid sequence according to SEQ ID NO: 1; (ii) a CDR2 having an amino acid sequence according to SEQ ID NO: 2; and (iii) a CDR3 having an amino acid sequence according to SEQ ID NO: 3; and B) a light chain variable region (VL) comprising an amino acid sequence at least 90% identical to the amino acid sequence set forth in SEQ ID NO: 12 and (i) a CDR1 having an amino acid sequence according to SEQ ID NO: 4; (ii) a CDR2 having an amino acid sequence according to SEQ ID NO: 5; and (iii) a CDR3 having an amino acid sequence according to SEQ ID NO: 6; and (b) a topoisomerase I inhibitor conjugated to the Nectin-2 antibody or antigen-binding fragment thereof using a linker.

2. The conjugate of claim 1, wherein the CDR2 of the VH has an amino acid sequence according to SEQ ID NO: 41.

3. The conjugate of claim 1, wherein the CDR1 of the VL has an amino acid sequence according to SEQ ID NO: 43.

4. The conjugate of claim 1, wherein the CDR2 of the VH has an amino acid sequence according to SEQ ID NO: 41, and the CDR1 of the VL has an amino acid sequence according to SEQ ID NO: 43.

5. A pharmaceutical composition comprising the conjugate of claim 1, and a pharmaceutically acceptable excipient, carrier, or diluent.

6. The conjugate of claim 1, wherein the topoisomerase I inhibitor is DXd.

* * * * *

SEQUENCE LISTING

Sequence total quantity: 71
SEQ ID NO: 1                  moltype = AA  length = 5
FEATURE                       Location/Qualifiers
source                        1..5
                              mol_type = protein
                              organism = unidentified

```
SEQUENCE: 1
SYWIH                                                                    5

SEQ ID NO: 2          moltype = AA  length = 16
FEATURE               Location/Qualifiers
source                1..16
                      mol_type = protein
                      organism = unidentified
VARIANT               16
                      note = X= KA or QG
SEQUENCE: 2
AVYPGNSDSN YNQKFX                                                        16

SEQ ID NO: 3          moltype = AA  length = 7
FEATURE               Location/Qualifiers
source                1..7
                      mol_type = protein
                      organism = unidentified
SEQUENCE: 3
LVGTFDY                                                                  7

SEQ ID NO: 4          moltype = AA  length = 11
FEATURE               Location/Qualifiers
source                1..11
                      mol_type = protein
                      organism = unidentified
VARIANT               1
                      note = X= K or R
VARIANT               11
                      note = X= V or A
SEQUENCE: 4
XASQNVGINV X                                                             11

SEQ ID NO: 5          moltype = AA  length = 7
FEATURE               Location/Qualifiers
source                1..7
                      mol_type = protein
                      organism = unidentified
SEQUENCE: 5
SASYRYS                                                                  7

SEQ ID NO: 6          moltype = AA  length = 9
FEATURE               Location/Qualifiers
source                1..9
                      mol_type = protein
                      organism = unidentified
SEQUENCE: 6
QQYNTNPFT                                                                9

SEQ ID NO: 7          moltype = AA  length = 8
FEATURE               Location/Qualifiers
source                1..8
                      mol_type = protein
                      organism = unidentified
SEQUENCE: 7
GYIFTSYW                                                                 8

SEQ ID NO: 8          moltype = AA  length = 8
FEATURE               Location/Qualifiers
source                1..8
                      mol_type = protein
                      organism = unidentified
SEQUENCE: 8
VYPGNSDS                                                                 8

SEQ ID NO: 9          moltype = AA  length = 9
FEATURE               Location/Qualifiers
source                1..9
                      mol_type = protein
                      organism = unidentified
SEQUENCE: 9
TKLVGTFDY                                                                9

SEQ ID NO: 10         moltype = AA  length = 6
FEATURE               Location/Qualifiers
source                1..6
                      mol_type = protein
                      organism = unidentified
SEQUENCE: 10
```

```
QNVGIN                                                                        6

SEQ ID NO: 11              moltype = AA  length = 116
FEATURE                    Location/Qualifiers
source                     1..116
                           mol_type = protein
                           organism = unidentified
SEQUENCE: 11
QVQLVQSGAE VKKPGSSVKV SCKASGYIFT SYWIHWVRQP PGKGLEWIGA VYPGNSDSNY   60
NQKFKARVTI TAVTSTSTAY MELSSLRSED TAVYYCTKLV GTFDYWGQGT TVTVSS       116

SEQ ID NO: 12              moltype = AA  length = 107
FEATURE                    Location/Qualifiers
source                     1..107
                           mol_type = protein
                           organism = unidentified
SEQUENCE: 12
DIQMTQSPST LSASVGDRVS VTCKASQNVG INVVWYQQKP GQPPKTLIYS ASYRYSGVPD   60
RFSGSGSGTD FTLTISSLQA EDLAEYFCQQ YNTNPFTFGQ GTKLEIK               107

SEQ ID NO: 13              moltype = AA  length = 116
FEATURE                    Location/Qualifiers
source                     1..116
                           mol_type = protein
                           organism = unidentified
SEQUENCE: 13
EVQLVQSGTE LKKPGSSVKV SCKASGYIFT SYWIHWVRQP PGKGLEWIGA VYPGNSDSNY   60
NQKFKARATI TAVTSTSTAY MELSSLTSED SAVYYCTKLV GTFDYWGQGT TVTVSS       116

SEQ ID NO: 14              moltype = AA  length = 116
FEATURE                    Location/Qualifiers
source                     1..116
                           mol_type = protein
                           organism = unidentified
SEQUENCE: 14
EVQLVQSGAE VKKPGSSVKV SCKASGYIFT SYWIHWVRQP PGKGLEWIGA VYPGNSDSNY   60
NQKFKARATI TAVTSTSTAY MELSSLRSED TAVYYCTKLV GTFDYWGQGT TVTVSS       116

SEQ ID NO: 15              moltype = AA  length = 116
FEATURE                    Location/Qualifiers
source                     1..116
                           mol_type = protein
                           organism = unidentified
SEQUENCE: 15
QVQLVQSGAE VKKPGSSVKV SCKASGYIFT SYWIHWVRQP PGKGLEWIGA VYPGNSDSNY   60
NQKFQGRVTI TAVTSTSTAY MELSSLRSED TAVYYCTKLV GTFDYWGQGT TVTVSS       116

SEQ ID NO: 16              moltype = AA  length = 116
FEATURE                    Location/Qualifiers
source                     1..116
                           mol_type = protein
                           organism = unidentified
SEQUENCE: 16
QVQLVQSGAE VKKPGSSVKV SCKASGYIFT SYWIHWVRQP PGKGLEWIGA VYPGNSDSNY   60
NQKFQGRVTI TADESTSTAY MELSSLRSED TAVYYCTKLV GTFDYWGQGT TVTVSS       116

SEQ ID NO: 17              moltype = AA  length = 107
FEATURE                    Location/Qualifiers
source                     1..107
                           mol_type = protein
                           organism = unidentified
SEQUENCE: 17
DIVMTQSPSF LSASVGDRVS VTCKASQNVG INVVWYQQRA GQPPKTLIYS ASYRYSGVPD   60
RFTGSGSGTD FTLTISSLQS EDLAEYFCQQ YNTNPFTFGQ GTKLEIK               107

SEQ ID NO: 18              moltype = AA  length = 107
FEATURE                    Location/Qualifiers
source                     1..107
                           mol_type = protein
                           organism = unidentified
SEQUENCE: 18
DIVMTQSPST LSASVGDRVS VTCKASQNVG INVVWYQQKP GQPPKTLIYS ASYRYSGVPD   60
RFTGSGSGTD FTLTISSLQA EDLAEYFCQQ YNTNPFTFGQ GTKLEIK               107

SEQ ID NO: 19              moltype = AA  length = 107
FEATURE                    Location/Qualifiers
source                     1..107
                           mol_type = protein
                           organism = unidentified
```

```
SEQUENCE: 19
DIQMTQSPST LSASVGDRVT ITCRASQNVG INVVWYQQKP GQPPKTLIYS ASYRYSGVPD  60
RFSGSGSGTD FTLTISSLQA EDVAVYYCQQ YNTNPFTFGQ GTKLEIK              107

SEQ ID NO: 20            moltype = AA  length = 107
FEATURE                  Location/Qualifiers
source                   1..107
                         mol_type = protein
                         organism = unidentified
SEQUENCE: 20
DIQMTQSPST LSASVGDRVT ITCRASQNVG INVAWYQQKP GQPPKTLIYS ASYRYSGVPD  60
RFSGSGSGTD FTLTISSLQA EDVAVYYCQQ YNTNPFTFGQ GTKLEIK              107

SEQ ID NO: 21            moltype = AA  length = 30
FEATURE                  Location/Qualifiers
source                   1..30
                         mol_type = protein
                         organism = unidentified
SEQUENCE: 21
QVQLVQSGAE VKKPGSSVKV SCKASGYIFT                                   30

SEQ ID NO: 22            moltype = AA  length = 14
FEATURE                  Location/Qualifiers
source                   1..14
                         mol_type = protein
                         organism = unidentified
SEQUENCE: 22
WVRQPPGKGL EWIG                                                    14

SEQ ID NO: 23            moltype = AA  length = 32
FEATURE                  Location/Qualifiers
source                   1..32
                         mol_type = protein
                         organism = unidentified
SEQUENCE: 23
RVTITAVTST STAYMELSSL RSEDTAVYYC TK                                32

SEQ ID NO: 24            moltype = AA  length = 11
FEATURE                  Location/Qualifiers
source                   1..11
                         mol_type = protein
                         organism = unidentified
SEQUENCE: 24
WGQGTTVTVS S                                                       11

SEQ ID NO: 25            moltype = AA  length = 30
FEATURE                  Location/Qualifiers
source                   1..30
                         mol_type = protein
                         organism = unidentified
SEQUENCE: 25
EVQLVQSGTE LKKPGSSVKV SCKASGYIFT                                   30

SEQ ID NO: 26            moltype = AA  length = 32
FEATURE                  Location/Qualifiers
source                   1..32
                         mol_type = protein
                         organism = unidentified
SEQUENCE: 26
RATITAVTST STAYMELSSL TSEDSAVYYC TK                                32

SEQ ID NO: 27            moltype = AA  length = 30
FEATURE                  Location/Qualifiers
source                   1..30
                         mol_type = protein
                         organism = unidentified
SEQUENCE: 27
EVQLVQSGAE VKKPGSSVKV SCKASGYIFT                                   30

SEQ ID NO: 28            moltype = AA  length = 32
FEATURE                  Location/Qualifiers
source                   1..32
                         mol_type = protein
                         organism = unidentified
SEQUENCE: 28
RATITAVTST STAYMELSSL RSEDTAVYYC TK                                32

SEQ ID NO: 29            moltype = AA  length = 32
FEATURE                  Location/Qualifiers
```

-continued

```
source                    1..32
                          mol_type = protein
                          organism = unidentified
SEQUENCE: 29
RVTITADEST STAYMELSSL RSEDTAVYYC TK                              32

SEQ ID NO: 30             moltype = AA   length = 23
FEATURE                   Location/Qualifiers
source                    1..23
                          mol_type = protein
                          organism = unidentified
SEQUENCE: 30
DIQMTQSPST LSASVGDRVS VTC                                        23

SEQ ID NO: 31             moltype = AA   length = 15
FEATURE                   Location/Qualifiers
source                    1..15
                          mol_type = protein
                          organism = unidentified
SEQUENCE: 31
WYQQKPGQPP KTLIY                                                 15

SEQ ID NO: 32             moltype = AA   length = 32
FEATURE                   Location/Qualifiers
source                    1..32
                          mol_type = protein
                          organism = unidentified
SEQUENCE: 32
GVPDRFSGSG SGTDFTLTIS SLQAEDLAEY FC                              32

SEQ ID NO: 33             moltype = AA   length = 10
FEATURE                   Location/Qualifiers
source                    1..10
                          mol_type = protein
                          organism = unidentified
SEQUENCE: 33
FGQGTKLEIK                                                       10

SEQ ID NO: 34             moltype = AA   length = 23
FEATURE                   Location/Qualifiers
source                    1..23
                          mol_type = protein
                          organism = unidentified
SEQUENCE: 34
DIVMTQSPSF LSASVGDRVS VTC                                        23

SEQ ID NO: 35             moltype = AA   length = 15
FEATURE                   Location/Qualifiers
source                    1..15
                          mol_type = protein
                          organism = unidentified
SEQUENCE: 35
WYQQRAGQPP KTLIY                                                 15

SEQ ID NO: 36             moltype = AA   length = 32
FEATURE                   Location/Qualifiers
source                    1..32
                          mol_type = protein
                          organism = unidentified
SEQUENCE: 36
GVPDRFTGSG SGTDFTLTIS SLQSEDLAEY FC                              32

SEQ ID NO: 37             moltype = AA   length = 23
FEATURE                   Location/Qualifiers
source                    1..23
                          mol_type = protein
                          organism = unidentified
SEQUENCE: 37
DIVMTQSPST LSASVGDRVS VTC                                        23

SEQ ID NO: 38             moltype = AA   length = 32
FEATURE                   Location/Qualifiers
source                    1..32
                          mol_type = protein
                          organism = unidentified
SEQUENCE: 38
GVPDRFTGSG SGTDFTLTIS SLQAEDLAEY FC                              32

SEQ ID NO: 39             moltype = AA   length = 23
```

-continued

```
FEATURE                 Location/Qualifiers
source                  1..23
                        mol_type = protein
                        organism = unidentified
SEQUENCE: 39
DIQMTQSPST LSASVGDRVT ITC                                                    23

SEQ ID NO: 40           moltype = AA  length = 32
FEATURE                 Location/Qualifiers
source                  1..32
                        mol_type = protein
                        organism = unidentified
SEQUENCE: 40
GVPDRFSGSG SGTDFTLTIS SLQAEDVAVY YC                                          32

SEQ ID NO: 41           moltype = AA  length = 17
FEATURE                 Location/Qualifiers
source                  1..17
                        mol_type = protein
                        organism = unidentified
SEQUENCE: 41
AVYPGNSDSN YNQKFKA                                                           17

SEQ ID NO: 42           moltype = AA  length = 17
FEATURE                 Location/Qualifiers
source                  1..17
                        mol_type = protein
                        organism = unidentified
SEQUENCE: 42
AVYPGNSDSN YNQKFQG                                                           17

SEQ ID NO: 43           moltype = AA  length = 11
FEATURE                 Location/Qualifiers
source                  1..11
                        mol_type = protein
                        organism = unidentified
SEQUENCE: 43
KASQNVGINV V                                                                 11

SEQ ID NO: 44           moltype = AA  length = 11
FEATURE                 Location/Qualifiers
source                  1..11
                        mol_type = protein
                        organism = unidentified
SEQUENCE: 44
KASQNVGINV A                                                                 11

SEQ ID NO: 45           moltype = AA  length = 11
FEATURE                 Location/Qualifiers
source                  1..11
                        mol_type = protein
                        organism = unidentified
SEQUENCE: 45
RASQNVGINV V                                                                 11

SEQ ID NO: 46           moltype = AA  length = 11
FEATURE                 Location/Qualifiers
source                  1..11
                        mol_type = protein
                        organism = unidentified
SEQUENCE: 46
RASQNVGINV A                                                                 11

SEQ ID NO: 47           moltype = AA  length = 446
FEATURE                 Location/Qualifiers
source                  1..446
                        mol_type = protein
                        organism = unidentified
SEQUENCE: 47
QVQLVQSGAE VKKPGSSVKV SCKASGYIFT SYWIHWVRQP PGKGLEWIGA VYPGNSDSNY   60
NQKFKARVTI TAVTSTSTAY MELSSLRSED TAVYYCTKLV GTFDYWGQGT TVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                        446

SEQ ID NO: 48           moltype = DNA  length = 1338
```

-continued

```
FEATURE           Location/Qualifiers
source            1..1338
                  mol_type = other DNA
                  organism = unidentified
SEQUENCE: 48
caggtgcagc tggtgcagag cggcgcggaa gtgaaaaaac cggggcagcag cgtgaaagtg   60
agctgcaaag cgagcggcta tattttttacc agctattgga ttcattgggt gcgccagccg  120
ccgggcaaag gcctggaatg gattggcgcg gtgtatccgg gcaacagcga tagcaactat  180
aaccagaaat ttaaagcgcg cgtgaccatt accgcggtga ccagcaccag caccgcgtat  240
atggaactga gcagcctgcg cagcgaagat accgcggtgt attattgcac caaactggtg  300
ggcacctttg attattgggg ccagggcacc accgtgaccg tgagcagcgc gagcaccaaa  360
ggcccgagcg tgtttccgct ggcgccgagc agcaaaagca ccagcggcgg caccgcggcg  420
ctgggctgcc tggtgaaaga ttattttccg aaccggtga  ccgtgagctg gaacagcggc  480
gcgctgacca gcggcgtgca tacctttccg gcggtgctgc agagcagcgg cctgtatagc  540
ctgagcagcg tggtgaccgt gccgagcagc agcctgggca cccagaccta tatttgcaac  600
gtgaaccata aaccgagcaa caccaaagtg gataaacgcg tggaaccgaa aagctgcgat  660
aaaacccata cctgcccgcc gtgccgggc  ccggaactgc tgggcggccc gagcgtgttt  720
ctgtttccgc cgaaaccgaa agataccctg atgattagcc gcaccccgga agtgacctgc  780
gtggtggtgg atgtgagcca tgaagatccg gaagtgaaat ttaactggta tgtggatggc  840
gtggaagtgc ataacgcgaa aaccaaaccg cgcgaagaac agtataacag cacctatcgc  900
gtggtgagcg tgctgaccgt gctgcatcag gattggctga acggcaaaga atataaatgc  960
aaagtgagca acaaagcgct gccggcgccg attgaaaaaa ccattagcaa agcgaaaggc  1020
cagccgcgcg aaccgcaggt gtatacctg  ccgccgagcc gcgaagaaat gaccaaaaac  1080
caggtgagcc tgacctgcct ggtgaaaggc ttttatccga gcgatattgc ggtggaatgg  1140
gaaagcaacg gccagccgga aaacaactat aaaaccaccc cgccggtgct ggatagcgat  1200
ggcagctttt ttctgtatag caaactgacc gtggataaaa gccgctggca gcagggcaac  1260
gtgtttagct gcagcgtgat gcatgaagcg ctgcataacc attatcccca gaaaagcctg  1320
agcctgagcc cgggcaaa                                                 1338

SEQ ID NO: 49       moltype = AA   length = 214
FEATURE             Location/Qualifiers
source              1..214
                    mol_type = protein
                    organism = unidentified
SEQUENCE: 49
DIQMTQSPST LSASVGDRVS VTCKASQNVG INVVWYQQKP GQPPKTLIYS ASYRYSGVPD   60
RFSGSGSGTD FTLTISSLQA EDLAEYFCQQ YNTNPFTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 50       moltype = DNA   length = 642
FEATURE             Location/Qualifiers
source              1..642
                    mol_type = other DNA
                    organism = unidentified
SEQUENCE: 50
gatattcaga tgacccagag cccgagcacc ctgagcgcga gcgtgggcga tcgcgtgagc   60
gtgacctgca aagcgagcca gaacgtgggc attaacgtgg tgtggtatca gcagaaaccg  120
ggccagccgc cgaaaaccct gatttatagc gcgagctatc gctatagcgg cgtgccggat  180
cgctttagcg gcagcggcag cggcaccgat tttaccctga ccattagcag cctgcaggcg  240
gaagatctgg cggaatattt ttgccagcag tataacacca acccgtttac ctttggccag  300
ggcaccaaac tggaaattaa acgcaccgtg gcggcgccga gcgtgtttat tttttccgccg  360
agcgatgaac agctgaaaag cggcaccgcg agcgtggtgt gcctgctgaa caacttttat  420
ccgcgcgaag cgaaagtgca gtggaaagtg ataacgcgc  tgcagagcgg caacagccag  480
gaaagcgtga ccgaacagga tagcaaagat agcacctata gcctgagcag caccctgacc  540
ctgagcaaag cggattatga aaaacataaa gtgtatgcgt gcgaagtgac ccatcagggc  600
ctgagcagcc cggtgaccaa aagctttaac cgcggcgaat gc                     642

SEQ ID NO: 51       moltype = DNA   length = 348
FEATURE             Location/Qualifiers
source              1..348
                    mol_type = other DNA
                    organism = unidentified
SEQUENCE: 51
caggtgcagc tggtgcagag cggcgcggaa gtgaaaaaac cggggcagcag cgtgaaagtg   60
agctgcaaag cgagcggcta tatttttacc agctattgga ttcattgggt gcgccagccg  120
ccgggcaaag gcctggaatg gattggcgcg gtgtatccgg gcaacagcga tagcaactat  180
aaccagaaat ttaaagcgcg cgtgaccatt accgcggtga ccagcaccag caccgcgtat  240
atggaactga gcagcctgcg cagcgaagat accgcggtgt attattgcac caaactggtg  300
ggcacctttg attattgggg ccagggcacc accgtgaccg tgagcagc               348

SEQ ID NO: 52       moltype = DNA   length = 348
FEATURE             Location/Qualifiers
source              1..348
                    mol_type = other DNA
                    organism = unidentified
SEQUENCE: 52
gaagtgcagc tggtgcagag cggcaccgaa ctgaaaaaac cggggcagcag cgtgaaagtg   60
agctgcaaag cgagcggcta tatttttacc agctattgga ttcattgggt gcgccagccg  120
```

-continued

```
ccgggcaaag gcctggaatg gattggcgcg gtgtatccgg gcaacagcga tagcaactat    180
aaccagaaat ttaaagcgcg cgcgaccatt accgcggtga ccagcaccag caccgcgtat    240
atggaactga gcagcctgac cagcgaagat agcgcggtgt attattgcac caaactggtg    300
ggcacctttg attattgggg ccagggcacc accgtgaccg tgagcagc                 348

SEQ ID NO: 53               moltype = DNA   length = 348
FEATURE                     Location/Qualifiers
source                      1..348
                            mol_type = other DNA
                            organism = unidentified
SEQUENCE: 53
gaagtgcagc tggtgcagag cggcgcggaa gtgaaaaaac cgggcagcag cgtgaaagtg    60
agctgcaaag cgagcggcta tattttttacc agctattgga ttcattgggt gcgccagccg   120
ccgggcaaag gcctggaatg gattggcgcg gtgtatccgg gcaacagcga tagcaactat    180
aaccagaaat ttaaagcgcg cgcgaccatt accgcggtga ccagcaccag caccgcgtat    240
atggaactga gcagcctgcg cagcgaagat accgcggtgt attattgcac caaactggtg    300
ggcacctttg attattgggg ccagggcacc accgtgaccg tgagcagc                 348

SEQ ID NO: 54               moltype = DNA   length = 348
FEATURE                     Location/Qualifiers
source                      1..348
                            mol_type = other DNA
                            organism = unidentified
SEQUENCE: 54
caggtgcagc tggtgcagag cggcgcggaa gtgaaaaaac cgggcagcag cgtgaaagtg    60
agctgcaaag cgagcggcta tattttttacc agctattgga ttcattgggt gcgccagccg   120
ccgggcaaag gcctggaatg gattggcgcg gtgtatccgg gcaacagcga tagcaactat    180
aaccagaaat ttcagggccg cgtgaccatt accgcggtga ccagcaccag caccgcgtat    240
atggaactga gcagcctgcg cagcgaagat accgcggtgt attattgcac caaactggtg    300
ggcacctttg attattgggg ccagggcacc accgtgaccg tgagcagc                 348

SEQ ID NO: 55               moltype = DNA   length = 348
FEATURE                     Location/Qualifiers
source                      1..348
                            mol_type = other DNA
                            organism = unidentified
SEQUENCE: 55
caggtgcagc tggtgcagag cggcgcggaa gtgaaaaaac cgggcagcag cgtgaaagtg    60
agctgcaaag cgagcggcta tattttttacc agctattgga ttcattgggt gcgccagccg   120
ccgggcaaag gcctggaatg gattggcgcg gtgtatccgg gcaacagcga tagcaactat    180
aaccagaaat ttcagggccg cgtgaccatt accgcggatg aaagcaccag caccgcgtat    240
atggaactga gcagcctgcg cagcgaagat accgcggtgt attattgcac caaactggtg    300
ggcacctttg attattgggg ccagggcacc accgtgaccg tgagcagc                 348

SEQ ID NO: 56               moltype = DNA   length = 321
FEATURE                     Location/Qualifiers
source                      1..321
                            mol_type = other DNA
                            organism = unidentified
SEQUENCE: 56
gatattcaga tgacccagag cccgagcacc ctgagcgcga gcgtgggcga tcgcgtgagc    60
gtgacctgca aagcgagcca gaacgtgggc attaacgtgg tgtggtatca gcagaaaccg    120
ggccagccgc cgaaaaccct gatttatagc gcgagctatc gctatagcgg cgtgccggat    180
cgctttagcg gcagcggcag cggcaccgat tttaccctga ccattagcag cctgcaggcg    240
gaagatctgc cggaatattt ttgccagcag tataacacca acccgtttac ctttggccag    300
ggcaccaaac tggaaattaa a                                              321

SEQ ID NO: 57               moltype = DNA   length = 321
FEATURE                     Location/Qualifiers
source                      1..321
                            mol_type = other DNA
                            organism = unidentified
SEQUENCE: 57
gatattgtga tgacccagag cccgagcttt ctgagcgcga gcgtgggcga tcgcgtgagc    60
gtgacctgca aagcgagcca gaacgtgggc attaacgtgg tgtggtatca gcagcgcgcg    120
ggccagccgc cgaaaaccct gatttatagc gcgagctatc gctatagcgg cgtgccggat    180
cgctttaccg gcagcggcag cggcaccgat tttaccctga ccattagcag cctgcagagc    240
gaagatctgc cggaatattt ttgccagcag tataacacca acccgtttac ctttggccag    300
ggcaccaaac tggaaattaa a                                              321

SEQ ID NO: 58               moltype = DNA   length = 321
FEATURE                     Location/Qualifiers
source                      1..321
                            mol_type = other DNA
                            organism = unidentified
SEQUENCE: 58
gatattgtga tgacccagag cccgagcacc ctgagcgcga gcgtgggcga tcgcgtgagc    60
gtgacctgca aagcgagcca gaacgtgggc attaacgtgg tgtggtatca gcagaaaccg    120
ggccagccgc cgaaaacccct gatttatagc gcgagctatc gctatagcgg cgtgccggat   180
```

-continued

```
cgctttaccg gcagcggcag cggcaccgat tttaccctga ccattagcag cctgcaggcg   240
gaagatctgg cggaatattt ttgccagcag tataacacca acccgtttac ctttggccag   300
ggcaccaaac tggaaattaa a                                             321

SEQ ID NO: 59              moltype = DNA   length = 321
FEATURE                    Location/Qualifiers
source                     1..321
                           mol_type = other DNA
                           organism = unidentified
SEQUENCE: 59
gatattcaga tgacccagag cccgagcacc ctgagcgcga gcgtgggcga tcgcgtgacc   60
attacctgcc gcgcgagcca gaacgtgggc attaacgtgg tgtggtatca gcagaaaccg   120
ggccagccgc cgaaaaccct gatttatagc gcgagctatc gctatagcgg cgtgccggat   180
cgctttagcg gcagcggcag cggcaccgat tttaccctga ccattagcag cctgcaggcg   240
gaagatgtgg cggtgtatta ttgccagcag tataacacca acccgtttac ctttggccag   300
ggcaccaaac tggaaattaa a                                             321

SEQ ID NO: 60              moltype = DNA   length = 321
FEATURE                    Location/Qualifiers
source                     1..321
                           mol_type = other DNA
                           organism = unidentified
SEQUENCE: 60
gatattcaga tgacccagag cccgagcacc ctgagcgcga gcgtgggcga tcgcgtgacc   60
attacctgcc gcgcgagcca gaacgtgggc attaacgtgg cgtggtatca gcagaaaccg   120
ggccagccgc cgaaaaccct gatttatagc gcgagctatc gctatagcgg cgtgccggat   180
cgctttagcg gcagcggcag cggcaccgat tttaccctga ccattagcag cctgcaggcg   240
gaagatgtgg cggtgtatta ttgccagcag tataacacca acccgtttac ctttggccag   300
ggcaccaaac tggaaattaa a                                             321

SEQ ID NO: 61              moltype = AA   length = 446
FEATURE                    Location/Qualifiers
source                     1..446
                           mol_type = protein
                           organism = unidentified
SEQUENCE: 61
QVQLVQSGAE VKKPGSSVKV SCKASGYIFT SYWIHWVRQP PGKGLEWIGA VYPGNSDSNY   60
NQKFKARVTI TAVTSTSTAY MELSSLRSED TAVYYCTKLV GTFDYWGQGT TVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELSGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                        446

SEQ ID NO: 62              moltype = AA   length = 446
FEATURE                    Location/Qualifiers
source                     1..446
                           mol_type = protein
                           organism = unidentified
SEQUENCE: 62
QVQLVQSGAE VKKPGSSVKV SCKASGYIFT SYWIHWVRQP PGKGLEWIGA VYPGNSDSNY   60
NQKFKARVTI TAVTSTSTAY MELSSLRSED TAVYYCTKLV GTFDYWGQGT TVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELSGGPSVF   240
LFPPKPKDTL MISRTPEVTC VVVDVSHEDP KVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                        446

SEQ ID NO: 63              moltype = AA   length = 446
FEATURE                    Location/Qualifiers
source                     1..446
                           mol_type = protein
                           organism = unidentified
SEQUENCE: 63
QVQLVQSGAE VKKPGSSVKV SCKASGYIFT SYWIHWVRQP PGKGLEWIGA VYPGNSDSNY   60
NQKFKARVTI TAVTSTSTAY MELSSLRSED TAVYYCTKLV GTFDYWGQGT TVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGIPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                        446

SEQ ID NO: 64              moltype = AA   length = 446
FEATURE                    Location/Qualifiers
source                     1..446
                           mol_type = protein
```

```
                              organism = unidentified
SEQUENCE: 64
QVQLVQSGAE VKKPGSSVKV SCKASGYIFT SYWIHWVRQP PGKGLEWIGA VYPGNSDSNY   60
NQKFKARVTI TAVTSTSTAY MELSSLRSED TAVYYCTKLV GTFDYWGQGT TVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGIPSVF  240
LFPPKPKDTL MISRTPEVTC VVVDVSHEDP IVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                       446

SEQ ID NO: 65             moltype = AA  length = 446
FEATURE                   Location/Qualifiers
source                    1..446
                          mol_type = protein
                          organism = unidentified
SEQUENCE: 65
QVQLVQSGAE VKKPGSSVKV SCKASGYIFT SYWIHWVRQP PGKGLEWIGA VYPGNSDSNY   60
NQKFKARVTI TAVTSTSTAY MELSSLRSED TAVYYCTKLV GTFDYWGQGT TVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGIPSVF  240
LFPPKPKDTL MISRTPEVTC VVRDVSHEDP EVKFNWYVDG VEVHNAKTKP REEQYNSTYR  300
VVSVLTVLHQ DWLNGKEYKC KVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                       446

SEQ ID NO: 66             moltype = AA  length = 396
FEATURE                   Location/Qualifiers
source                    1..396
                          mol_type = protein
                          organism = unidentified
SEQUENCE: 66
QVQLVQSGAE VKKPGSSVKV SCKASGYIFT SYWIHWVRQP PGKGLEWIGA VYPGNSDSNY   60
NQKFKARVTI TAVTSTSTAY MELSSLRSED TAVYYCTKLV GTFDYWGQGT TVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKAEPKSCD KTHTCPPCPA PELLGGPSVF  240
LFPPKPKDTL MISRTPEVTC VVVDVSHRDP EVKFNWYVDG VEVHNAKTKP REEQYNSTYR  300
VVSVLTVLHQ DWLNGKEYKC AVSNKALPAP IEKTISKAKG QPREPQVYTL PPSRDELTKN  360
QVSLTCLVKG FYPSDIAVEW ESNGQPENNY KTTPPV                            396

SEQ ID NO: 67             moltype = AA  length = 446
FEATURE                   Location/Qualifiers
source                    1..446
                          mol_type = protein
                          organism = unidentified
SEQUENCE: 67
QVQLVQSGAE VKKPGSSVKV SCKASGYIFT SYWIHWVRQP PGKGLEWIGA VYPGNSDSNY   60
NQKFKARVTI TAVTSTSTAY MELSSLRSED TAVYYCTKLV GTFDYWGQGT TVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PEAAGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALGAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                       446

SEQ ID NO: 68             moltype = AA  length = 443
FEATURE                   Location/Qualifiers
source                    1..443
                          mol_type = protein
                          organism = unidentified
SEQUENCE: 68
QVQLVQSGAE VKKPGSSVKV SCKASGYIFT SYWIHWVRQP PGKGLEWIGA VYPGNSDSNY   60
NQKFKARVTI TAVTSTSTAY MELSSLRSED TAVYYCTKLV GTFDYWGQGT TVTVSSASTK  120
GPSVFPLAPC SRSTSESTAA LGCLVKDYFP EPVTVSWNSG ALTSGVHTFP AVLQSSGLYS  180
LSSVVTVPSS SLGTKTYTCN VDHKPSNTKV DKRVESKYGP PCPPCPAPEF PGGPSVFLFP  240
PKPKDTLMIS RTPEVTCVVR DVSQEDPEVQ FNWYVDGVEV HNAKTKPREE QFNSTYRVVS  300
VLTVLHQDWL NGKEYKCKVS NKGLPSSIEK TISKAKGQPR EPQVYTLPPS QEEMTKNQVS  360
LTCLVKGFYP SDIAVEWESN GQPENNYKTT PPVLDSDGSF FLYSRLTVDK SRWQEGNVFS  420
CSVMHEALHN HYTQKSLSLS LGK                                          443

SEQ ID NO: 69             moltype = AA  length = 442
FEATURE                   Location/Qualifiers
source                    1..442
                          mol_type = protein
                          organism = unidentified
SEQUENCE: 69
QVQLVQSGAE VKKPGSSVKV SCKASGYIFT SYWIHWVRQP PGKGLEWIGA VYPGNSDSNY   60
NQKFKARVTI TAVTSTSTAY MELSSLRSED TAVYYCTKLV GTFDYWGQGT TVTVSSASTK  120
GPSVFPLAPC SRSTSESTAA LGCLVKDYFP EPVTVSWNSG ALTSGVHTFP AVLQSSGLYS  180
```

```
LSSVVTVPSS NFGTQTYTCN VDHKPSNTKV DKTVERKCCV ECPPCPAPPV AGHSVFLFPP   240
KPKDTLMISR TPEVTCVVVD VSHEDPEVQF NWYVDGVEVH NAKTKPREEQ FNSTFRVVSV   300
LTVVHQDWLN GKEYKCKVSN KGLPAPIEKT ISKTKGQPRE PQVYTLPPSR EEMTKNQVSL   360
TCLVKGFYPS DISVEWESNG QPENNYKTTP PMLDSDGSFF LYSKLTVDKS RWQQGNVFSC   420
SVMHEALHNH YTQKSLSLSP GK                                            442

SEQ ID NO: 70            moltype = AA  length = 442
FEATURE                  Location/Qualifiers
source                   1..442
                         mol_type = protein
                         organism = unidentified
SEQUENCE: 70
QVQLVQSGAE VKKPGSSVKV SCKASGYIFT SYWIHWVRQP PGKGLEWIGA VYPGNSDSNY    60
NQKFKARVTI TAVTSTSTAY MELSSLRSED TAVYYCTKLV GTFDYWGQGT TVTVSSASTK   120
GPSVFPLAPC SRSTSESTAA LGCLVKDYFP EPVTVSWNSG ALTSGVHTFP AVLQSSGLYS   180
LSSVVTVPSS NFGTQTYTCN VDHKPSNTKV DKTVERKCCV ECPPCPAPPV AGHSVFLFPP   240
KPKDTLMISR TPEVTCVVRD VSHEDPEVQF NWYVDGVEVH NAKTKPREEQ FNSTFRVVSV   300
LTVVHQDWLN GKEYKCKVSN KGLPAPIEKT ISKTKGQPRE PQVYTLPPSR EEMTKNQVSL   360
TCLVKGFYPS DISVEWESNG QPENNYKTTP PMLDSDGSFF LYSKLTVDKS RWQQGNVFSC   420
SVMHEALHNH YTQKSLSLSP GK                                            442

SEQ ID NO: 71            moltype = AA  length = 19
FEATURE                  Location/Qualifiers
source                   1..19
                         mol_type = protein
                         organism = unidentified
SEQUENCE: 71
MGWSCIILFL VATATGVHS                                                 19
```